US006610518B2

(12) United States Patent
Pacey

(10) Patent No.: US 6,610,518 B2
(45) Date of Patent: Aug. 26, 2003

(54) ENZYMATIC OXIDATIONS

(75) Inventor: Michael Stephen Pacey, County of Kent (GB)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 64 days.

(21) Appl. No.: 09/867,347

(22) Filed: May 29, 2001

(65) Prior Publication Data

US 2002/0012977 A1 Jan. 31, 2002

Related U.S. Application Data

(60) Provisional application No. 60/220,285, filed on Jul. 24, 2000.

(30) Foreign Application Priority Data

May 31, 2000 (GB) .............................................. 0013368

(51) Int. Cl.⁷ .......................... C12P 17/00; C12P 17/16; C12P 1/04; C12N 9/00
(52) U.S. Cl. ....................... 435/117; 435/118; 435/121; 435/170; 435/189
(58) Field of Search ................................ 435/117, 118, 435/121, 189, 170

(56) References Cited

FOREIGN PATENT DOCUMENTS

| DE | 2202410 | 1/1972 |
|----|---------|--------|
| EP | 0658548 | 6/1995 |
| WO | 9947693 | 9/1999 |

OTHER PUBLICATIONS

T. Omura; Forty Years of Cytochrome P450; Biochemical and Biophysical Research Communications; 266:690–698 (1999).
Johnson, et al.; Microbial Oxygenation of Dialkylbenzenes (I); Bioorganic Chemistry; 2:99–110 (1973).
Abstract JP–60258173.
Cerniglia, et al.; Transformation of 1– and 2–Methylnaphthalene by Cunninghamella Elegans; Applied and Environmental Microbiology; 47:111–118 (1984).
Holland, et al.; Biotransformation of Organic Sulfides; Tetrahedron Asymm.; vol. 5, No. 7, pp. 1241–1248 (1994).
Schwartz, et al.; Microbial Oxidation of Ebastine; Appl. Microbiol. Biotechnol; 44:731–735 (1996).

*Primary Examiner*—Herbert J. Lilling
(74) *Attorney, Agent, or Firm*—Paul H. Ginsburg; Martha G. Munchhof; Kohn & Associates, PLLC

(57) ABSTRACT

The following invention relates to a process for oxidizing alkyl groups attached directly or via a linker, to a sulfonamide moiety (II) by the use of cytochrome P450 enzymes, to give the corresponding alcohol or carboxylic acid (I).

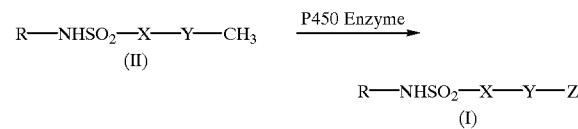

wherein R is an organic radical, X is a linker, Y is $-C(CH_3)_2-$ or $-CH(CH_3)-$ and Z is $-CH_2OH$ or $-COOH$.

40 Claims, No Drawings

ENZYMATIC OXIDATIONS

CROSS REFERENCE TO RELATED APPLICATIONS

This application claims the benefit of priority of foreign application GB 0013368.6 filed in Great Britain on May 31, 2000. This application also claims the benefit of priority of U.S. Provisional Application No. 60/220,285 filed Jul. 24, 2000.

The following invention relates to a process for oxidising alkyl groups attached directly or via a linker, to a sulfonamide moiety by the use of a cytochrome P450 enzyme.

There are a large number of structurally complex molecules of interest to medicinal chemists, which possess a hydroxylated or carboxylated alkyl group, attached directly or via a linker, to a sulfonamide group. The synthesis of these molecules is complicated by the synthetic steps necessary to hydroxylate or carboxylate such alkyl groups whilst avoiding-undesirable side reactions.

This problem has been solved by the process of the present invention, which teaches the use of a cytochrome P450 enzyme to selectively oxidise an alkyl group attached directly or via a linker to a sulfonamide group. The process which is specific and tolerant of other functional groups in the molecule allows the synthetic chemist to introduce a hydroxy or carboxy group into the synthesis of a molecule at a late stage, in a one step process. This reduces the overall number of steps required to synthesise medicinally important molecules and so improves the efficiency of their preparation.

The term 'Cytochrome P450' is used to describe a superfamily of hemoprotein enzymes. They are characterised by the absorption band of their $Fe^{II}$—CO complex form which has an absorption maxima at 447–452 nm, indicative of a thiolate ligated hemoprotein. They are also called heme-thiolate proteins, though this category is much wider than just cytochrome P450. Cytochrome P450 appear to have diversified from a common ancestor and they may be found in almost all forms of living organism, from animals and plants to fungi and bacteria, where they carry out the role of an oxygenase.

Cytochrome P450 catalysed reactions are known to produce a range of metabolites. The reactions may usually be classified as one of three types:
a) Hydroxylation, the insertion of an oxygen atom between the H atom and some other heavier atom such as carbon or nitrogen,
b) Epoxidation, the addition of an oxygen atom to a carbon-carbon double bond,
c) Heteroatom oxidation, the addition of an oxygen atom to the electron pair on a heteroatom.

They are also known to catalyse reduction reactions. Useful reviews of the cytochrome P450 enzyme are provided in Handbook of Drug metabolism, Ed. Thomas Woolf, Publisher Marcel Decker, ISBN 0824702298, March 1999, chap 4, p109 and by T. Omura, Biochemical and Biophysical Research Communications, 1999, 266, 690.

R. A. Johnson et al., Bioogameric Chemistry, 1973, 2, 99, discloses the treatment of a number of dialkylbenzenes with the P450 enzyme containing microorganism *Sporotrichum sulfurescens*, to form an alcohol on the alkyl side chain.

The abstract of JP-60258173 discloses the synthesis of an α-(3-t-butyl-5-hydroxy-t-butylbenzylidene)butyrolactone by microbial hydroxylation of the corresponding t-butyl precursor. Suitable microorganisms for the transformation are those from the Mucor and Aspergillus strains.

C. Cerniglia et al., Applied and Environmental Microbiology, 1984, 47, 111, discloses the transformation of 1- and 2-methylnaphthalene by *Cunninghamella elegans* into the corresponding hydroxymethyl derivative. A small amount of further metabolites were also isolated in which the product had been further oxidised to the carboxylic acid or where hydroxylation of the ring system had taken place.

H. L. Holland et al., Tetrahedron Asymm., 1994, 5, 1241, teaches the oxidation of chiral para substituted alkyl benzyl sulfides to the sulfoxide. In cases where the para substituent was i-propyl or t-butyl, hydroxylation at the terminal methyl of the alkyl group was seen, as well as oxidation of the sulfide. In the case of the i-propyl group, the corresponding sulfone was also seen. These transformations were conducted using the microorganism Helminthosporium NRRL-4671.

H. Schwartz et al., Appl. Microbiol. Biotechnol., 1994, 44, 731, investigates the microbial oxidation of ebastine to carebastine. Of 15 microorganisms examined, only the Cunninghamella strains provided the desired biotransformation.

WO-A-99/47693 discloses a method for making fexofenadine from terfenadine by a biotransformation performed using a microorganism culture of the genus Streptomyces at a pH ranging between 5 and 8.

The oxidation by a cytochrome P450 enzyme of alkyl groups attached directly, or via a linker, to a sulfonamide moiety, is new. Sulfonamides are known to exhibit antimicrobial activity. Accordingly, molecules containing a sulfonamide group have not been viewed as suitable candidates for use in a biotransformation process as it was thought they would kill any microorganism used. Surprisingly, it has now been found that molecules containing a sulfonamide group may be used in certain oxidative biotransformations.

According to a first aspect of the present invention there is provided a process for synthesising the compounds of formula (I)

wherein
R is an organic radical;
X is selected from
a) a 5- or 6-membered monocyclic aromatic ring optionally containing one or two heteroatoms, each independently selected from O, N and S;
b) a $C_1$–$C_6$ alkylene group, straight chain or branched chain; and
c) a direct link;
Y is —C(CH$_3$)$_2$— or —CH(CH$_3$)—; and
Z is —CH$_2$OH or —COOH;
which comprises oxidising a compound of formula (II)

wherein
R, X and Y are as defined above, with a cytochrome P450 enzyme.

The process described may be used to oxidise a suitable alkyl group to the corresponding hydroxy or carboxy derivative. These oxidations proceed from the alkyl to the hydroxy and in the latter case, onwards from the hydroxy to the corresponding carboxylic acid. It will be appreciated that by careful manipulation of the reaction conditions, one may selectively isolate a product at the desired oxidation level and maximise the yield of the desired product. The oxidation may be stopped at the hydroxy derivative or allowed to continue onwards to the carboxylic acid. To produce the corresponding carboxylic acid no modification to the process is required other than that the process be given sufficient time to further oxidise the substrate. It should be noted that the nature of the R substituent may influence the speed of the reaction and hence the yields of the desired products. Whilst all P450 enzymes are considered suitable for conducting the disclosed invention, certain microorganisms will be particularly suitable for specific levels of oxidation.

This transformation is effected by a cytochrome P450 enzyme. Particularly favoured are microorganisms which contain the P450 enzyme. Preferred microorganisms are unicellular bacteria, exemplified by species such as *Escherichia coli*, filamentous bacteria exemplified by such strains as Actinomyces and Streptomyces and filamentous fungi. Suitable microorganisms are specifically noted in this text by their name and the American Type Culture Collection (ATCC) number assigned to them when deposited with a recognised International Depository Authority under the terms of the Budapest Treaty. Three new microorganisms were identified as being effective in this transformation and deposits were made with the American Type Culture Collection in Manassas, USA, under the terms of the Budapest Treaty. All three are gram positive filamentous bacteria, belonging to the Actinomycetales: Streptomyces species PTA-1685, *Streptomyces cyaneus* PTA-1686 and *Streptomyces lydicus* PTA-1687 and were cultivated on quarter strength ATCC172 agar slope.

The new microorganisms assigned Accession Numbers PTA-1685, PTA-1686 and PTA-1687 were all deposited with the ATCC at 10801 University Boulevard, Manassas, Va., 20110-2209, USA, on Apr. 11, 2000.

In a preferred embodiment X is selected from:

a) a 5- or 6-membered monocyclic aromatic ring optionally containing one or two heteroatoms, each independently selected from O, N and S; and b) a $C_1$–$C_6$ alkylene group, straight chain or branched chain;

When X is as defined in (a) above, X may suitably be phenylene or a 5 or 6 membered aromatic heterocycle containing 1 heteroatom selected from O, N and S. Particularly suitably X may be phenylene or a 6 member aromatic heterocycle containing 1 heteroatom selected from O, N and S. Most suitably X is phenylene or pyridylene.

When X is as defined in (b) above, X may suitably be a $C_{2-4}$ alkylene group, straight chain or branched chain. Most suitably X is ethylene or propylene.

It is believed that this process is specific to the oxidation of alkyl groups, attached directly or via a linker to a sulfonamide moiety, and that this reaction will be tolerated by a wide range of R groups. Accordingly R may encompass all organic radicals. Preferably, R is a 5- or 6-membered monocyclic aromatic ring optionally containing one or two heteroatoms, each independently selected from O, N and S, said ring being optionally further substituted. Particularly preferred is a 5- or 6-membered monocyclic aromatic ring containing two heteroatoms, each independently selected from O and N, said ring being optionally further substituted. Most preferred are substituted pyrazoles, substituted pyrimidines and substituted isoxazoles. The invention has been utilised with a variety of differing R substituents; suitable R substituents include:

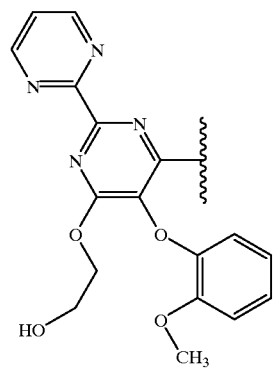

4-(2-hydroxyethoxy)-5-(2-methoxyphenoxy)-2-(2-pyrimidinyl) pyrimidin-6-yl

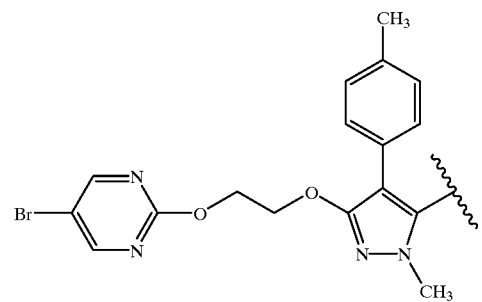

3-[2-(5-bromopyrimidin-2-yl)-oxyethoxy]-1-methyl-4-p-tolylpyrazol-5-yl

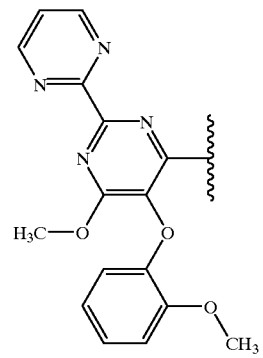

4-methoxy-5-(2-methoxyphenoxy)-2-(2-pyrimidinyl) pyrimidin-6-yl

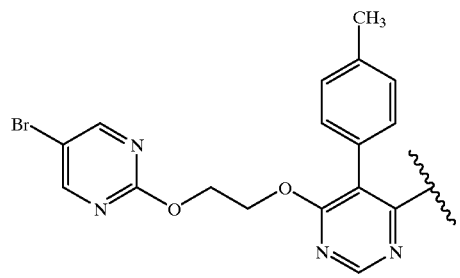

4-[2-(5-bromopyrimidin-2-yl)oxyethoxy] 5-p-tolylpyrimidin-6-yl

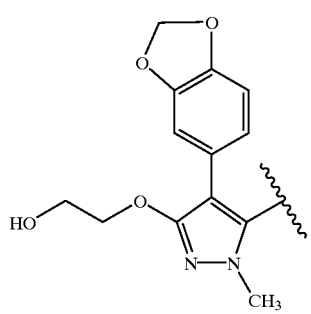

4-(1,3-benzodioxol-5-yl)-3-(2-hydroxyethoxy)-1-methylpyrazol-5-yl

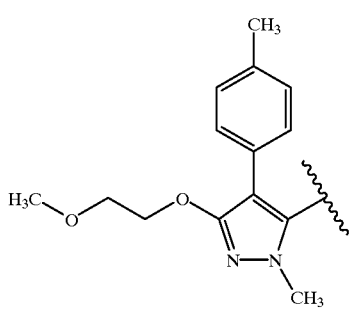

3-(2-methoxyethoxy)-1-methyl-4-p-tolylpyrazol-5-yl

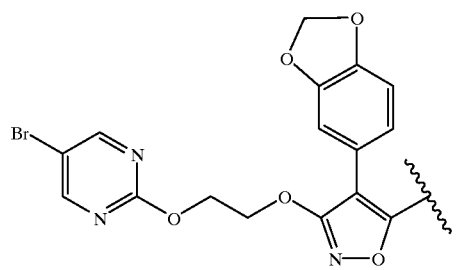

4-(1,3-benzodioxol-5-yl)-3-[2-(5-bromopyrimidin-2-yl)oxyethoxy]
isoxazol-5-yl

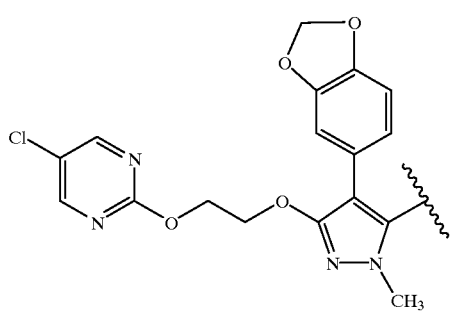

4-(1,3-benzodioxol-5-yl)-3-[2-(5-chloropyrimidin-2-yl)
oxyethoxy]-1-methylpyrazol-5-yl

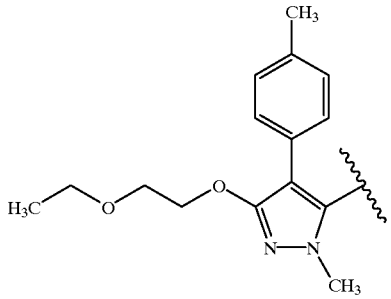

3-(2-ethoxyethoxy)-1-methyl-4-p-tolypyrzaol-5-yl

One embodiment of the present invention is a process for making compounds of formula (I) when Z is —CH$_2$OH, Y is —C(CH$_3$)$_2$— and X and R are as defined for formula According to this embodiment, preferably X is phenylene, pyridylene, ethylene or propylene; most preferably X is 1,4-phenylene.

According to this embodiment R is preferably selected from one of:

3-[2-(5-bromopyrimidin-2-yl)oxyethoxy]-1-methyl-4-p-tolylpyrazol-5-yl

4-[2-(5-bromopyrimidin-2-yl)oxyethoxy]-5-p-tolylpyrimidin-6-yl 4-(2-hydroxyethoxy)-5-(2-methoxyphenoxy)-2-(2-pyrimidinyl)pyrimidin-6-yl 4-methoxy-5-(2-methoxyphenoxy)-2-(2-pyrimidinyl)pyrimidin-6-yl 3-(2-ethoxyethoxy)-1-methyl-4-p-tolylpyrazol-5-yl 4-(1,3-benzodioxol-5-yl)-3-[2-(5-chloropyrimidin-2-yl)oxyethoxy]-1-methylpyrazol-5-yl 4-(1,3-benzodioxol-5-yl)-3-(2-hydroxyethoxy)-1-methylpyrazol-5-yl 4-(1,3-benzodioxol-5-yl)-3-[2-(5-bromopyrimidin-2-yl)oxyethoxy]isoxazol-5-yl Most preferably R is 4-[2-(5-bromopyrimidin-2-yl)oxyethoxy]-5-p-tolylpyrimidin-6-yl.

In this embodiment of the invention, micro-organisms particularly suitable for use in the process include: *Streptomyces lavendulae* ATCC14159, Streptomyces sp. PTA-1685, *Streptomyces cyaneus* PTA-1686, *Streptomyces lydicus* PTA-1687, *Streptomyces griseus* ATCC55070, *Streptomyces griseolus* ATCC11796, *Amyclatopsis orientalis* ATCC19795, *Streptomyces griseus* subsp. *griseus* ATCC13273, *Streptomyces argentolus* ATCC11009, *Nocardia meditteranei* ATCC21271, *Streptomyces fumanus* ATCC19904, *Amycolata autotrophica* ATCC35203, *Streptomyces rimosus* subsp. *rimosus* ATCC10970, *Streptomyces griseus* subsp. *griseus* ATCC10137, Streptomyces sp. ATCC31273, *Cunninghamella echinulata* var. *elegans*

ATCC8688a, *Mortierella isabellina* ATCC42613, *Verticillium lecanii* ATCC60540, *Mucor circinelloides* ATCC7941, *Cunninghamella echinulata* var. *echinulata* ATCC36190, *Syncephalastrum racemosum* ATCC18192, *Beauvaria sulphurescens* ATCC7159, *Absidia pseudocylindrospora* ATCC24169, *Amycolata autotrophica* ATCC13181, *Rhodococcus rhodochrous* ATCC12674, *Rhodococcus rhodochrous* ATCC19067, *Bacillus megaterium* ATCC14581, *Bacillus megaterium* ATCC13368, *Rhodococcus* sp. ATCC19070, *Actinomyces* sp. ATCC53828, *Bacillus subtilis* ATCC55060, *Pseudomonas putida* ATCC17453, *Pseudomonas putida* ATCC49451, *Bacillus sphaericus* ATCC10208, *Rhizopus oryzae* ATCC11145, *Absidia blakesleeeana* ATCC10148a, *Sepedonium chrysospermum* ATCC13378, *Alcaligenes eutrophus* ATCC17697, *Streptomyces galilaeus* ATCC31133, *Actinoplanes missouriensis* ATCC23342, *Actinoplanes missouriensis* ATCC14538, *Streptomyces peucetius* subsp. *caesius* ATCC27952, *Streptomyces lincolnensis* ATCC25466, *Streptomyces bambergiensis* ATCC13879, *Streptomyces argillaceus* ATCC12956, *Streptomyces albogriseolus* ATCC31422, *Streptomyces rutgersensis* ATCC3350, *Corynebacterium hydrocarboxydans* ATCC21767, *Streptomyces fradiae* ATCC 10745, *Streptomyces hydrogenans* ATCC19631, Unidentified bacterium ATCC13930, *Actinoplanes* sp. ATCC53771, *Thamnidium elegans* ATCC18191, *Aspergillus terreus* ATCC10020, *Curvularia lunata* ATCC13432, *Emericella unguis* ATCC13431, *Epicoccum humicola* ATCC12722, *Rhodococcus chlorophenolicus* ATCC49826, *Aspergillus ochraceus* ATCC18500, *Pithomyces cynodontis* ATCC26150, *Streptomyces roseochromogenes* ATCC13400, *Streptomyces griseus* subsp. *autotrophica* ATCC53668, *Streptomyces griseus* subsp. *griseus* ATCC23337, *Absidia repens* ATCC14849 and *Aspergillus alliaceus* ATCC10060.

Preferred microorganisms for this embodiment where R is 3-[2-(5-bromopyrimidin-2-yl)oxyethoxy]-1-methyl-4-p-tolylpyrazol-5-yl include: *Syncephalastrum racemosum* ATCC18192, Streptomyces sp. PTA-1685, *Streptomyces lavendulae* ATCC14159, *Streptomyces cyaneus* PTA-1686, *Streptomyces griseus* ATCC55070, *Amycolatopsis orientalis* ATCC19795, *Streptomyces argentolus* ATCC11009, *Nocardia meditteranei* ATCC21271, *Streptomyces fumanus* ATCC19904, *Streptomyces rimosus* subsp. *rimosus* ATCC10970, *Streptomyces griseus* ATCC10137, *Cunninghamella echinulata* ATCC8688a, *Mortierella isabellina* ATCC42613, *Verticillium lecanii* ATCC60540, *Mucor circinelloides* ATCC7941 and *Cunninghamella echinulata* ATCC 10028b.

Preferred microorganisms for this embodiment where R is 4-[2-(5-bromopyrimidin-2-yl)oxyethoxy]-5-p-tolylpyrimidin-6-yl include: *Streptomyces lavendulae* ATCC14159, Streptomyces sp. PTA-1685, *Streptomyces cyaneus* PTA-1686, *Streptomyces lydicus* PTA-1687, *Streptomyces griseus* ATCC55070, *Streptomyces griseolus* ATCC11796, *Amyclatopsis orientalis* ATCC19795, *Streptomyces griseus* subsp. *griseus* ATCC13273, *Streptomyces fumanus* ATCC19904, *Amycolata autotrophica* ATCC35203, *Streptomyces griseus* subsp. *griseus* ATCC10137, Streptomyces sp. ATCC31273, *Mortierella isabellina* ATCC42613, *Veticillium lecanii* ATCC60540, *Mucor circimelloides* ATCC7941, *Cunninghamella achinulata* var. *echinulata* ATCC36190, *Syncephalastrum racemosum* ATCC18192, *Amycolata autotrophica* ATCC13181, *Rhodococcus rhodochrous* ATCC12674, *Rhodococcus rhodochrous* ATCC19067, *Bacillus megaterium* ATCC14581, *Bacillus megaterium* ATCC13368, *Rhodococcus* sp. ATCC19070, *Actinomyces* sp. ATCC53828, *Bacillus subtilis* ATCC55060, *Pseudomonas putida* ATCC49451, *Bacillus sphaericus* ATCC10208, *Rhizopus oryzae* ATCC11145, *Absidia blakesleeeana* ATCC10148a, *Sepedonium chrysospermum* ATCC13378, *Alcaligenes eutrophus* ATCC17697, *Streptomyces galilaeus* ATCC31133, *Actinoplanes missouriensis* ATCC23342, *Actinoplanes missouriensis* ATCC14538, *Streptomyces peucetius* subsp. *caesius* ATCC27952, *Streptomyces lincolnensis* ATCC25466, *Streptomyces bambergiensis* ATCC13879, *Streptomyces argillaceus* ATCC12956, *Streptomyces albogriseolus* ATCC31422, *Streptomyces rutgersensis* ATCC3350, *Corynebacterium hydrocarboxydans* ATCC21767, *Streptomyces fradiae* ATCC10745, *Streptomyces hydrogenans* ATCC19631, Unidentified bacterium ATCC13930, *Actinoplanes* sp. ATCC53771, *Thamnidium elegans* ATCC18191, *Aspergillus terreus* ATCC10020, *Curvularia lunata* ATCC13432, *Emericella unguis* ATCC13431 *Epicoccum humicola* ATCC12722, *Rhodococcus chlorophenolicus* ATCC49826, *Aspergillus ochraceus* ATCC18500, *Streptomyces roseochromogenes* ATCC13400, *Streptomyces griseus* subsp. *autotrophica* ATCC53668, *Streptomyces griseus* subsp. *griseus* ATCC23337, *Absidia repens* ATCC14849 and *Aspergillus alliaceus* ATCC10060.

Preferred microorganisms for this embodiment where R is 4-(2-hydroxyethoxy)-5-(2-methoxyphenoxy)-2-(2-pyrimidinyl)pyrimidin-6-yl include: *Streptomyces rimosus* subsp. *rimosus* ATCC10970, *Streptomyces fumanus* ATCC19904, *Streptomyces argentolus* ATCC11009, *Bacillus megaterium* ATCC14538, *Streptomyces griseus* ATCC13273, *Streptomyces griseus* ATCC10137, *Streptomyces griseolus* ATCC11796, *Streptomyces lavendulae* ATCC14159, *Streptomyces cyaneus* PTA-1686, Streptomyces sp. PTA-1685, *Amycolata autotrophica* ATCC13181, *Amycolata autotrophica* ATCC35203 and *Mortierella isabellina* ATCC42613.

Preferred micro-organisms for this embodiment where R is 4-(1,3-benzodioxol-5-yl)-3-[2-(5-bromopyrimid-2-yl)oxyethoxy]isoxazol-5-yl include: *Streptomyces rimosus* subsp. *rimosus* ATCC10970, *Streptomyces fumanus* ATCC19904, *Streptomyces argentolus* ATCC11009, *Bacillus megaterium* ATCC14538, *Streptomyces griseus* ATCC13273, *Streptomyces griseus* ATCC10137, *Streptomyces griseolus* ATCC11796, *Streptomyces lavendulae* ATCC14159, *Streptomyces cyaneus* PTA-1686, Streptomyces sp. PTA-1685, *Amycolata autotrophica* ATCC13181, *Amycolata autotrophica* ATCC35203 and *Mortierella isabellina* ATCC42613.

Another embodiment of this aspect of the present invention is a process for making compounds of formula I when Z is —CH$_2$OH, Y is —CH(CH$_3$)— and X and R are as defined in formula (I).

According to this embodiment, preferably X is phenylene, pyridylene, ethylene or propylene; most preferably X is 2,5-pyridylene, wherein Y is at the 2-position.

According to this embodiment, R is preferably 4-(1,3-benzodioxol-5-yl)-3-[2-(5-chloropyrimidin -2-yl) oxyethoxy]-1-methylpyrazol-5-yl.

Micro-organisms particularly suitable for use in this embodiment include: *Streptomyces lavendulae* ATCC14159, Streptomyces sp. PTA-1685, *Streptomyces cyaneus* PTA-1686, *Streptomyces lydicus* PTA-1687, *Streptomyces griseus* ATCC55070, *Streptomyces griseolus* ATCC11796, *Amyclatopsis orientalis* ATCC19795, *Streptomyces griseus* subsp. *griseus* ATCC13273, *Streptomyces argentolus* ATCC11009, *Nocardia meditteranei* ATCC21271, *Streptomyces fumanus* ATCC19904, *Amycolata autotrophica* ATCC35203, *Streptomyces rimosus* subsp.

rimosus ATCC10970, *Streptomyces griseus* subsp. *griseus* ATCC10137, Streptomyces sp. ATCC31273, *Cunninghamella echinulata* var. *elegans* ATCC8688a, *Mortierella isabellina* ATCC42613, *Verticillium lecanii* ATCC60540, *Mucor circinelloides* ATCC7941, *Cunninghamella echinulata* var. *echinulata* ATCC36190, *Syncephalastrum racemosum* ATCC18192, *Beauvaria sulphurescens* ATCC7159, *Absidia pseudocylindrospora* ATCC24169, *Amycolata autotrophica* ATCC13181, *Rhodococcus rhodochrous* ATCC12674, *Rhodococcus rhodochrous* ATCC19067, *Bacillus megaterium* ATCC14581, *Bacillus megaterium* ATCC13368, Rhodococcus sp. ATCC19070, Actinomyces sp. ATCC53828, *Bacillus subtilis* ATCC55060, *Pseudomonas putida* ATCC17453, *Pseudomonas putida* ATCC49451, *Bacillus sphaericus* ATCC10208, *Rhizopus oryzae* ATCC11145, *Absidia blakesleeeana* ATCC10148a, *Sepedonium chrysospermum* ATCC13378, *Alcaligenes eutrophus* ATCC17697, *Streptomyces galilaeus* ATCC31133, *Actinoplanes missouriensis* ATCC23342, *Actinoplanes missouriensis* ATCC14538, *Streptomyces peucetius* subsp. *caesius* ATCC27952, *Streptomyces lincolnensis* ATCC25466, *Streptomyces bambergiensis* ATCC13879, *Streptomyces argillaceus* ATCC12956, *Streptomyces albogriseolus* ATCC31422, *Streptomyces rutgersensis* ATCC3350, *Corynebacterium hydrocarboxydans* ATCC21767, *Streptomyces fradiae* ATCC10745, *Streptomyces hydrogenans* ATCC19631, Unidentified bacterium ATCC13930, Actinoplanes sp. ATCC53771, *Thamnidium elegans* ATCC18191, *Aspergillus terreus* ATCC10020, *Curvularia lunata* ATCC13432, *Emericella unguis* ATCC13431, *Epicoccum humicola* ATCC12722, *Rhodococcus chlorophenolicus* ATCC49826, *Aspergillus ochraceus* ATCC18500, *Pithomyces cynodontis* ATCC26150, *Streptomyces roseochromogenes* ATCC13400, *Streptomyces griseus* subsp. *autotrophica* ATCC53668, *Streptomyces griseus* subsp. *griseus* ATCC23337, *Absidia repens* ATCC14849 and *Aspergillus alliaceus* ATCC10060.

The oxidation of the alkyl group to the corresponding hydroxy derivative using a P450 enzyme may be allowed to continue onwards to the carboxylic acid. No modification to the process is required other than that the process be given sufficient time to further oxidise the substrate. It will be appreciated that by careful manipulation of the reaction conditions, one may selectively isolate a product at the desired oxidation level and maximise the yield of the desired product. Further, the nature of the R substituent may influence the speed of the reaction and hence the yields of the desired products. Whilst all P450 enzymes are considered suitable for conducting the disclosed invention, certain microorganisms will be particularly suitable for specific levels of oxidations.

Another embodiment of the present invention is a process for making compounds of formula (I) when Z is —COOH, Y is —C(CH$_3$)$_2$— and X and R are as defined in formula (I).

In this embodiment, preferably X is phenylene, pyridylene, ethylene or propylene; most preferably X is 1,4-phenylene.

According to this embodiment, R is preferably selected from one of;

3-[2-(5-bromopyrimidin-2-yl)oxyethoxy]-1-methyl-4-p-tolylpyrazol-5-yl
4-[2-(5-bromopyrimidin-2-yl)oxyethoxy]-5-p-tolylpyrimidin-6-yl
1-methyl-3-(2-methoxyethoxy)-4-p-tolylpyrazol-5-yl
3-(2-ethoxyethoxy)-1-methyl-4-p-tolylpyrazol-5-yl.
Most preferably R is 4-[2-(5-bromopyrimidin-2-yl)oxyethoxy]-5-p-tolylpyrimidin-6-yl.

Microorganisms particularly suitable for use in this embodiment include: *Amycolata autotrophica* ATCC 35203, *Nocardia meditteranei* ATCC21271, *Amycolatopsis orientalis* ATCC19795 *Streptomyces griseolus* ATCC11796, *Streptomyces rimosus* subsp. *rimosus* ATCC10970 and *Nocardia meditteranei* ATCC21271.

Preferred microorganisms for this embodiment where R is 3-[2-(5-bromopyrimidin-2-yl)oxyethoxy]-1-methyl-4-p-tolylpyrazol-5-yl include: *Amycolata autotrophica* ATCC 35203, *Nocardia meditteranei* ATCC21271 and *Amycolatopsis orientalis* ATCC19795

Preferred micro-organisms for this embodiment where R is 4-[2-(5-bromopyrimidin-2-yl)oxyethoxy]-5-p-tolylpyrimidin-6-yl include: *Streptomyces griseolus* ATCC 11796, *Streptomyces rimosus* subsp. *rimosus* ATCC10970 and *Nocardia meditteranei* ATCC21271.

A further embodiment of the present invention is a process for making compounds of formula (I) when Z is —COOH, Y is —CH(CH$_3$)— and X and R are as defined in formula (I).

According to this embodiment, preferably X is phenylene, pyridylene, ethylene or propylene; most preferably X is 2,5-pyridylene.

Microorganisms particularly suitable for use in this embodiment include *Amycolata autotrophica* ATCC 35203, *Nocardia meditteranei* ATCC21271, *Amycolatopsis orientalis* ATCC19795 *Streptomyces griseolus* ATCC11796, *Streptomyces rimosus* subsp. *rimosus* ATCC10970 and *Nocardia meditteranei* ATCC21271.

The introduction of a functional group into a complex molecule that already possesses a wide range of functionality is extremely difficult. Unless one has absolute specificity it is likely that the reaction will be accompanied by a host of competing side reactions. The effect of this is to produce the desired compound in a smaller yield and to provide difficulties in extracting and purifying the desired molecule. These problems are particularly acute in the case of oxidising a C—H bond. This is almost impossible to achieve selectively using standard chemical means.

To avoid this problem, the skilled synthetic chemist will employ a careful retrosynthetic analysis of the synthetic target. The synthetic strategy will involve avoiding side reactions and will usually involve a protecting group strategy. In avoiding conflicting side reactions, the chemist will be forced to add extra reaction steps to his synthesis, e.g. protection and deprotection.

These extra steps are undesirable. There are the additional costs of the reagents, solvents and other manufacturing costs. The extra steps will also depress the overall yield, again adding to the cost of the final product. Further there are the problems associated with purifying the compound after each step and disposing of any pollutants.

The process of the present invention solves these problems by introducing a hydroxy or carboxy moiety into a molecule with great specificity in one step with high yield. So specific is the process, that such moieties may be introduced at a very late stage, into a molecule with a multiplicity of other functionality. The advantage of this process are that fewer synthetic steps are required leading to lower costs in reagents, solvents and production costs. Further there will be fewer pollutants resulting in less environmental damage and clean up costs. The process is also suitable for production on an industrial scale.

Microorganisms containing these P450 cytochrome enzymes suitable for use in this invention may be obtained from a variety of sources. They may be isolated from various soil samples, then grown on various agars as described in the ATCC Catalogue of Bacteria and Bacteriophages, 18th Edition, 1992, or the ATCC Catalogue of Fungi and Yeasts, 17th Edition, 1987.

The processes of the invention may be carried out in any suitable aqueous fermentation medium.

It will be appreciated that the process of the present invention may be conducted in the presence of various additives such as solubilisers such as alcohols and dipolar aprotic solvents, e.g. methanol and dimethylsulfoxide.

The wide range of functionality able to tolerate the process of the present invention is exemplified in the following examples;

High performance liquid chromatography (HPLC) retention times and UV spectra were recorded using a Hewlett-Packard 1090 LUSI diode-array spectrophotometer (method A). All NMR spectra were measured in $CDCl_3$ or MeOD by an Inova 300 MHz or 400 MHz spectrometer unless otherwise indicated and peak positions are expressed in parts per million (ppm) downfield from tetramethylsilane. The peak shapes are denoted as follows: s, singlet; d, doublet; t, triplet; q, quartet; m, multiplet; br broad. High resolution MS data was acquired on a AutoSpecQ with electrospray ionisation (ESI) or thermospray ionisation (TSPI) using a PEG reference (or on a Bruker Apex II FTMS with ESI where indicated).

Infra red data was collected on a Perkin Elmer Paragon 1000 FT-IR using conventional techniques such as a polyethylene (PE) film or as a NUJOL dispersion on sodium chloride (NaCl) discs. Peak positions are expressed in $cm^{-1}$.

HPLC-MS data was acquired using a Hewlett-Packard 1090M liquid chromatograph interfaced to a VG platform II mass spectrometer equipped with an ES source (method B).

| HPLC method A: | |
|---|---|
| Column | Beckman Ultrasphere ™ 5 micron ODS 4 mm × 25 cm |
| Mobile Phase | Linear gradient: methanol:water (65:35) to methanol:water (95:5) over 40 minutes |
| Flow rate | 0.85 ml/min |

| HPLC-MS method B: | |
|---|---|
| Column | Phenomenex Magellan ™ 5 micron ODS 4.6 mm × 15 cm |
| Mobile Phase | Gradient: 0.1% v/v trifluoroacetic acid (TFA) in water:acetonitrile (90:10) to 0.1% TFA in water:acetonitrile (2:98) over 5 minutes, maintain 0.1% TFA in water:acetonitrile (2:98) 5 to 11.5 minutes. |
| Flow rate | 0.85 ml/min |

Use is made of the following fermentation media.

| AS-7H inoculum medium | |
|---|---|
| Cornstarch (Hidex ™) | 20 g |
| Cotton Seed Meal (Pharmamedia ™) | 15 g |
| Ardamine pH ™ | 5 g |
| Calcium carbonate | 2 g |
| Tap water | 1 l |
| NaOH | To pH 7.2 |

| AP-5H Production Medium | |
|---|---|
| Cornststarch | 80 g |
| Yeast extract (Oxoid ™) | 5 g |
| $K_2HPO_4$ | 1 g |
| $MgSO_4.7H_2O$ | 1 g |
| Glutamic acid | 1 g |
| $FeSO_4.7H_2O$ | 0.01 g |
| $ZnSO_4.2H_2O$ | 0.001 g |
| $MnSO_4.H_2O$ | 0.001 g |
| $CaCO_3$ | 7 g |
| Tap water | 1 l |
| NaOH | To pH 7.0 |

| MY Inoculum and Production Medium | |
|---|---|
| Glucose | 10 g |
| Peptone (Difco ™) | 5 g |
| Yeast extract (Oxoid ™) | 3 g |
| Malt extract (Oxoid ™) | 5 g |
| Tap water | 1 l |
| NaOH | To pH 6.3–6.5 |

| Tomato Inoculum and Production Medium | |
|---|---|
| Tomato Paste | 40 g |
| Corn Steep Liquor | 2.5 g |
| Oats | 10 g |
| Cerelose | 10 g |
| $FeSO_4.7H_2O$ | 0.001 g |
| $ZnSO_4.2H_2O$ | 0.001 g |
| $MnSO_4.H_2O$ | 0.001 g |
| Demineralised Water | 1 l |
| NaOH | To pH 6.8 |

EXAMPLE 1

Preparation and Isolation of N-[3-{2-[(5-bromo-2-pyrimidinyl)oxy]ethoxy}-1-methyl-4-(4-methylphenyl)-1H-pyrazol-5-yl]-4-(2-hydroxy-1,1-dimethylethyl)benzenesulfonamide

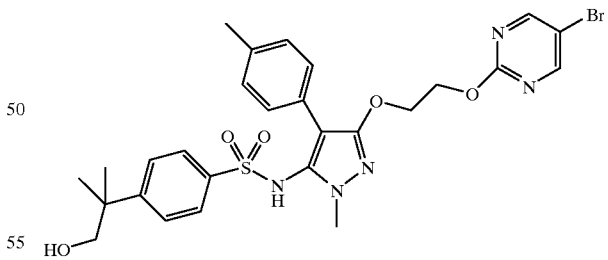

*Streptomyces rimosus* subsp. *rimosus* ATCC10970 maintained on a quarter strength ATCC172 agar slope was inoculated as a loopful of spores into a 300 ml Erlenmeyer flask containing 50 ml of AS-7H inoculum medium. This was allowed to incubate for 2 days at 28° C., 200 rpm on an Infors Multitron™ Shaker with 1" throw. 2 mls of this inoculum medium was then transferred to each of sixteen 300 ml Erlenmeyer flask containing 50 ml of AP-5H production medium and incubated under the same conditions for a further 24 hours. At this point 20 mg of N-[3-{2-[(5-bromo-2-pyrimidinyl)oxy]ethoxy}-1-methyl-4-(4-methylphenyl)-1H-pyrazol-5-yl]-4-(tert-butyl)benzenesulfonamide (GB Patent Application No 9917858.4) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 1.4 g.

The crude extract was purified by preparative reversed phase HPLC with a Phenomenex Magellen™ 5μ C18 column (150 mm×21.2 mm) in three injections. Using a gradient mobile phase of 35:65 to 20:80 (0.1% trifluoroacetic acid in water):methanol from 1.5 to 20 minutes at a flow rate of 20 ml/min, the product was eluted at 11.4 min. The fractionation was repeated with another three injections using a gradient mobile phase of 35:65 to 20:80 water:methanol at a flow rate of 20 ml/min. The compound of interest eluted again at 11.4 min and the product fractions were concentrated under reduced pressure to yield the title compound as a colourless amorphous solid (53.5 mg).

HPLC retention time—Method A; 11.3 minutes.

$\delta_H$ (300 MHz, CDCl$_3$)(selected nmr data) 8.45 (2H, s); 7.40 (2H, d); 7.15 (1H, s); 7.10 (2H, d); 6.80 (4H, s); 4.65 (2H, m); 4.55 (2H, m); 3.80 (3H, s); 3.50 (2H,s); 2.20 (3H, s); 1.15 (6H, s)

m/z (ESI) [M+H]$^+$=616.1216, C$_{27}$H$_{31}$BrN$_5$O$_5$S requires 616.1229 m/z (ESI) [M+Na]$^+$–638.1060, C$_{27}$H$_{30}$BrN$_5$O$_5$SNa requires 638.1049

EXAMPLE 2

Preparation and Isolation of 2-[4-({[3-{2-[(5-bromo-2-pyrimidinyl)oxy]ethoxy}-1-methyl-4-(4-methylphenyl)-1H-pyrazol-5-yl]amino}sulfonyl)phenyl]-2-methylpropanoic acid

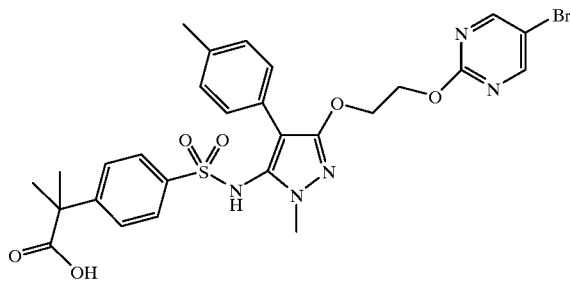

*Amycolata autotrophica* ATCC35203 maintained on a quarter strength ATCC172 agar slope was inoculated as a loopful of spores into five 300 ml Erlenmeyer flasks each containing 50 mm of MY inoculum medium. This was allowed to incubate for 2 days at 28° C., 200 rpm on an Infors Multitron™ Shaker with 1" throw. Two mls of this inoculum was then transferred to each of sixty 300 mm Erlenmeyer flask containing 50 mm of MY production medium and incubated under the same conditions for a further 24 hours. At this point 20 mg of N-[3-{2-[(5-bromo-2-pyrimidinyl)oxy]ethoxy)}-1-methyl-4-(4-methylphenyl)-1H-pyrazol-5-yl]-4-(tert-butyl)benzenesulfonamide (GB Patent Application No 9917858.4) dissolved in 0.5 mm of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 2.0 g.

The crude extract was purified by preparative reversed phase HPLC with a Phenomenex Magellen™ 5μ C18 column (150 mm×21.2 mm) in six injections. Using a gradient mobile phase of 35:65 to 20:80 water:methanol from 1.5 to 20 minutes at a flow rate of 20 mm/min, the product was eluted at 12.5 min. The product fractions were concentrated under reduced pressure to yield the title compound as a colourless amorphous solid (213.4 mg).

HPLC retention time—Method A; 11.5 minutes.

$\delta_H$ (300 MHz, CDCl$_3$)(selected nmr data) 8.65 (2H, s); 7.15 (4H, m); 6.95 (2H, d); 6.90 (s, 1H); 6.70 (2H, d); 4.65 (2H, m); 4.45 (2H, m); 3.90 (3H, s); 2.30 (3H, s); 1.55 (6H, s)

m/z (ESI) [M+H]$^+$=630.1005, C$_{27}$H$_{29}$BrN$_5$O$_6$S requires 630.1022 m/z (ESI) [M+Na]$^+$=652.0842, C$_{27}$H$_{28}$BrN$_5$O$_6$SNa requires 652.0841

$\nu_{max}$ (NaCl, film) 3241, 2976, 1710, 1572, 1551, 1427, 1327, 1167, 1085

EXAMPLE 3

Preparation of N-[6-{2-[(5-bromo-2-pyrimidinyl)oxy]ethoxyl}-5-(4-methylphenyl)-4-pyrimidinyl]-4-(2-hydroxy-1,1-dimethylethyl)benzenesulfonamide

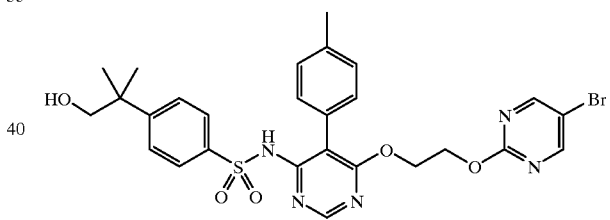

*Streptomyces rimosus* subsp. *rimosus* ATCC10970 maintained on a quarter strength ATCC172 agar slope was inoculated as a loopful of spores into a 300 mm Erlenmeyer flask containing 50 mm of AS-7H inoculum medium. This was allowed to incubate for 2 days at 28° C., 200 rpm on an Infors Multitron™ Shaker with 1" throw. 2 mls of this inoculum medium was then transferred to each of six 300 mm Erlenmeyer flask containing 50 mm of AP-5H production medium and incubated under the same conditions for a further 24 hours. At this point 5 mg of N-[6-{2-[(5-bromo-2-pyrimidinyl)oxy]ethoxy}-5-(4-methylphenyl)-4-pyrimidinyl]-4-(tert-butyl)benzenesulfonamide (EP 0658548B1) dissolved in 0.5 mm of dimethylsulfoxide was added to each of the flasks and the fermentation allowed to continue under the same conditions for a further 3 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 col-

15 umn (150 mm×21.2 mm). Using a gradient mobile phase of 60:40 to 5:95 water:acetonitrile from 2 to 14 minutes at a flow rate of 20 mm/min, the product was eluted at 8.0 min. The product fractions were concentrated under reduced pressure to yield the title compound as a colourless amorphous solid (1.45 mg).

HPLC retention time—Method A; 12.5 minutes.

$\delta_H$ (300 MHz, CDCl$_3$)(selected nmr data) 8.45 (2H, s); 8.40 (1H, s); 8.05 (2H, d); 7.55 (2H, d); 7.20 (2H, d); 7.10 (2H, d); 4.65 (2H, m); 4.60, (2H, m); 3.65 (2H, s); 2.40 (3H, s); 1.35 (6H, s)

m/z (ESI, FTMS) [M+H]$^+$=614.1066, C$_{27}$H$_{29}$BrN$_5$O$_5$S requires 614.1068

EXAMPLE 4

Preparation of 2-[4-({[6-{2-[(5-bromo-2-pyrimidinyl)oxy]ethoxy}-5-(4-methylphenyl)-4-pyrimidinyl]amino}sulfonyl)phenyl]-2-methylpropanoic acid

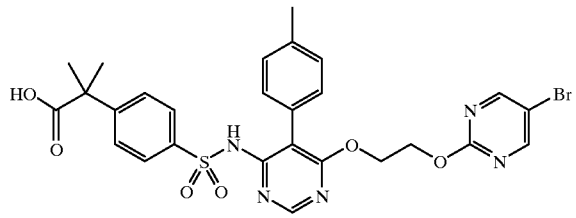

*Streptomyces rimosus* subsp. *rimosus* ATCC10970 maintained on a quarter strength ATCC172 agar slope was inoculated as a loopful of spores into a 300 mm Erlenmeyer flask containing 50 mm of AS-7H inoculum medium. This was allowed to incubate for 2 days at 28° C., 200 rpm on an Infors Multitron™ Shaker with 1" throw. 2 mls of this inoculum medium was then transferred to each of six 300 ml Erlenmeyer flask containing 50 ml of AP-5H production medium and incubated under the same conditions for a further 24 hours. At this point 5 mg of N-[6-{2-[(5-bromo-2-pyrimidinyl)oxy]ethoxy}-5-(4-methylphenyl)-4-pyrimidinyl]-4-(tert-butyl)benzenesulfonamide dissolved in 0.5 ml of dimethylsulfoxide (EP 0658548B1) was added to each of the flasks and the fermentation allowed to continue under the same conditions for a further 3 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5µ C18 column (150 mm×21.2 mm). Using a gradient mobile phase of 60:40 to 5:95 water:acetonitrile from 2 to 14 minutes at a flow rate of 20 ml/min, the product was eluted at 7.0 min. The product fractions were concentrated under reduced pressure to yield a colourless amorphous solid (1.3 mg).

HPLC retention time—Method A; 12.4 minutes.

$\delta_H$ (300 MHz, CDCl$_3$)(selected nmr data) 8.55 (2H, s); 8.40 (1H, s); 7.85 (2H, d); 7.45 (2H, d) 7.20 (2H, d); 6.95(2H, d); 4.65 (2H, m); 4.55 (2H, m); 2.40 (3H, s); 1.60 (6H, s)

m/z (ESI) [M+H]$^+$=630.0833 C$_{27}$H$_{26}$BrN$_5$O$_6$S requires 630.1980

EXAMPLE 5

Preparation of N-[6-{2-[(5-bromo-2-pyrimidinyl)oxy]ethoxy}-5-(4-methylphenyl)-4-pyrimidinyl]-4-(2-hydroxy-1,1-dimethylethyl)benzenesulfonamide

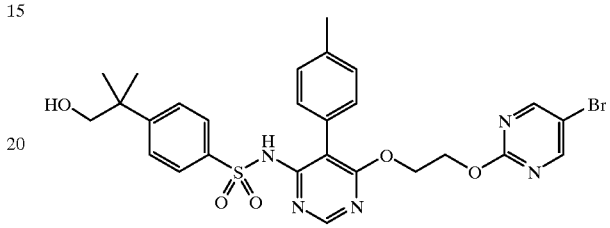

*Syncephalastrum racemosum* ATCC18192 maintained on a potato dextrose agar slope was inoculated as a loopful of spores into a 300 ml Erlenmeyer flask containing 50 ml of Tomato medium. This was allowed to incubate for 2 days at 28° C., 200 rpm on an Infors Multitron™ Shaker with 1" throw. At this point 3 mg of N-[{6-2-[(5-bromo-2-pyrimidinyl)oxy]ethoxy}-5-(4-methylphenyl)-4-pyrimidinyl]-4-(tert-butyl)benzenesulfonamide (EP 0658548B1) dissolved in 0.5 ml of dimethylsulfoxide was added to the flask and the fermentation allowed to continue under the same conditions for a further 24 hours. The flask was then extracted with 200 mls of ethyl acetate and the combined ethyl acetate solubles concentrated to dryness to give a gum solid.

The crude extract was purified by preparative reversed phase HPLC with a Phenomenex Magellen™ 5µ C18 column (150 mm×21.2 mm). Using a gradient mobile phase of 50:50 to 5:95 water:acetonitrile from 2 to 14 minutes at a flow rate of 20 ml/min, the product was eluted at 5.1 min. The product fractions were concentrated under reduced pressure to yield the title compound as a colourless amorphous white solid (1.3 mg).

HPLC retention time—Method A; 12.5 minutes.

$\delta_H$ (300 MHz, CDCl$_3$)(selected nmr data) 8.45 (2H, s); 8.40 (1H, s); 8.05 (2H, d); 7.55 (2H, d); 7.20 (2H, d); 7.10 (2H, d); 4.65 (2H, m); 4.60 (2H, m); 3.65 (2H, s) 2.40 (3H, s); 1.35 (6H, s)

m/z (ESI, FTMS) [M+H]$^+$614.1059, C$_{27}$H$_{29}$BrN$_5$O$_5$S requires 614.1068

EXAMPLE 6

Preparation of the N-[4-(2-hydroxyethoxy)-5-(2-methoxyphenoxy)-2-(2-pyrimidinyl)pyrimidin-6-yl]-4-(2-hydroxy-1,1-dimethylethyl)benzenesulphonamide

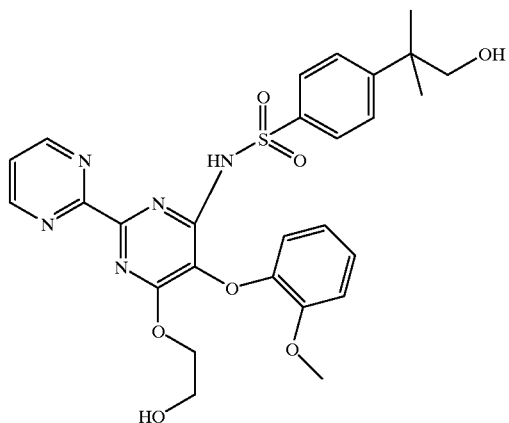

*Streptomyces rimosus* subsp. *rimosus* ATCC10970 maintained on a quarter strength ATCC172 agar slope was inoculated as a loopful of spores into a 300 ml Erlenmeyer flask containing 50 ml of AS-7H inoculum medium. This was allowed to incubate for 2 days at 28° C., 200 rpm on an Infors Multitron™ Shaker with 1" throw. 2 mls of this inoculum medium was then transferred to one 300 ml Erlenmeyer flask containing 50 ml of AP-5H production medium and incubated under the same conditions for a further 24 hours. At this point 1 mg of 4-tert butyl-N-[4-(2-hydroxyethoxy)-5-(2-methoxyphenoxy)-2-(2-pyrimidinyl)pyrimidin-6-yl]benzenesulphonamide (CA 2071193) dissolved in 0.5 ml of dimethylsulfoxide was added to each of the flasks and the fermentation allowed to continue under the same conditions for a further 24 hours. The flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm). Using a gradient mobile phase of 60:40 to 5:95 water:acetonitrile from 2 to 14 minutes at a flow rate of 20 mm/min, the product was eluted at 10.9 min. The product fractions were concentrated under reduced pressure to yield the title compound as a colourless amorphous solid (0.5 mg).

HPLC retention time—Method B; 4.7 minutes.

$\delta_H$ (400 MHz, CDCl$_3$)(selected nmr data) 9.20 (2H, br s); 8.35 (2H, m); 7.65 (1H, br s); 7.45 (2H, m); 7.10 (2H, m); 6.95 (1H, m); 6.90 (1H, m); 4.65 (2H, m); 3.90 (3H, s); 3.85 (2H, m); 3.60 (2H, s); 1.30 (6H, s)

m/z (ESI, FTMS) [M+H]$^+$=568.1834, C$_{27}$H$_{30}$N$_5$O$_7$S requires 568.1860

EXAMPLE 7

Preparation of 4-hydroxy-N-[6-methoxy-5-(2-methoxyphenoxy)-2-(2-pyrimidinyl)-pyrimidin-4-yl]-3,3-dimethyl-1-butanesulfonamide

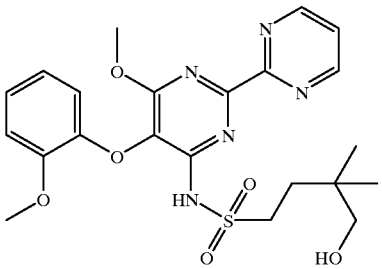

*Streptomyces rimosus* subsp. *rimosus* ATCC10970 maintained on a quarter strength ATCC172 agar slope was inoculated as a loopful of spores into a 300 ml Erlenmeyer flask containing 50 ml of AS-7H inoculum medium. This was allowed to incubate for 2 days at 28° C., 200 rpm on an Infors Multitron™ Shaker with 1" throw. 2 mls of this inoculum medium was then transferred to twenty six 300 ml Erlenmeyer flask containing 50 ml of AP-5H production medium and incubated under the same conditions for a further 24 hours. At this point 4.5 mg of N-[6-methoxy-5-(2-methoxyphenoxy)-2-(2-pyrimidinyl)-4-pyrimidinyl]-3,3-dimethyl-1-butanesulfonamide (Preparation 1) dissolved in 0.5 ml of methanol was added to each of the flasks and the fermentation allowed to continue under the same conditions for a further 20 hours. The flask was then extracted with 200 mls of ethyl acetate and the combined ethyl acetate solubles concentrated to dryness to give a gum solid, 430 mg .

The crude extract was purified by preparative reversed phase HPLC with a Phenomenex Magellen™ 5μ C18 column (150 mm×21.2 mm) in four injections. Using a gradient mobile phase of 85:15 to 15:85 water/methanol from 0 to 25 minutes at a flow rate of 20 ml/min, the product was eluted at 15.0 minutes. The product fractions were concentrated under reduced pressure to yield the title compound as a colourless amorphous solid (42.4 mg).

HPLC retention time—Method A; 9.3 minutes.

$\delta_H$ (300 MHz, CD$_3$OD) 8.90 (2H, d); 7.50 (1H, t); 7.00 (1H, d); 6.90 (1H, t); 6.75 (1H, t); 6.60 (1H, d); 3.95 (3H, s); 3.90 (3H, s); 3.35 (2H, m); 3.15 (2H, s); 1.60 (2H, m); 0.75 (6H, s)

m/z (ESI, FTMS) [M+H]$^+$=490.1745, C$_{22}$H$_{28}$N$_5$O$_6$S requires 490.1755

$\nu_{max}$ (PE) 3406, 2920, 2850, 1582, 1563, 1501, 1473, 1426, 1386, 1132

EXAMPLE 8

Preparation of 5-hydroxy-N-[6-methoxy-5-(2-methoxyphenoxy)-2-(2-pyrimidinyl)-4-pyrimidinyl]-4,4-dimethyl-1-pentanesulfonamide

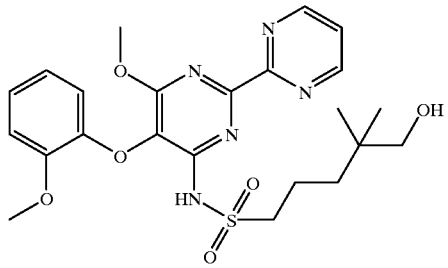

*Streptomyces rimosus* subsp. *rimosus* ATCC10970 maintained on a quarter strength ATCC172 agar slope was inoculated as a loopful of spores into a 300 ml Erlenmeyer flask containing 50 ml of AS-7H inoculum medium. This was allowed to incubate for 2 days at 28° C., 200 rpm on an Infors Multitron Shaker with 1" throw. 2 mls of this inoculum medium was then transferred to twenty 300 ml Erlenmeyer flask containing 50 ml of AP-5H production medium and incubated under the same conditions for a further 24 hours. At this point 4.5 mg of N-[6-methoxy-5-(2-methoxyphenoxy)-2-(2-pyrimidinyl)-4-pyrimidinyl]-4,4-dimethyl-1-pentanesulfonamide (Preparation 3) dissolved in 0.5 ml of methanol was added to each of the flasks and the fermentation allowed to continue under the same conditions for a further 20 hours. The flask was then extracted with 200 mls of ethyl acetate and the combined ethyl acetate solubles concentrated to dryness to give a gum solid, 200 mg.

The crude extract was purified by preparative reversed phase HPLC with a Phenomenex Magellen™ 5μ C18 column (150 mm×21.2 mm) in four injections. Using a gradient mobile phase of 90:10 to 40:60 water:acetonitrile from 3 to 20 minutes at a flow rate of 20 ml/min, the product was eluted at 17.2 minutes. The product fractions were concentrated under reduced pressure to yield the title compound as a colourless amorphous solid (46.7 mg).

HPLC retention time—Method A; 11.3 minutes.

$\delta_H$ (300 MHz, CDCl$_3$)(selected nmr data) 8.95 (2H, d); 7.40 (1H, m); 7.05 (2H, m); 6.95 (1H, m); 6.85 (1H, m); 4.15 (3H, s); 3.95 (3H, s); 3.85 (2H, m); 3.25 (2H, s); 1.80 (2H, m); 1.40 (2H, m); 0.80 (6H, s)

m/z (ESI) [M+H]$^+$=504.1927, C$_{23}$H$_{30}$N$_5$O$_6$S requires 504.1917 m/z (ESI) [M+Na]$^+$=526.1749, C$_{23}$H$_{29}$N$_5$O$_6$SNa requires 526.1736

$\nu_{max}$ (PE) 3390, 3219, 2955, 1583, 1558, 1503, 1388, 1336, 1253, 1092, 875, 748

EXAMPLE 9

Preparation of 4-(2-hydroxy-1,1-dimethylethyl)-N-[6-methoxy-5-(2-methoxyphenoxy)-2-(2-pyrimidinyl)-4-pyrimidin-4-yl]benzenesulfonamide

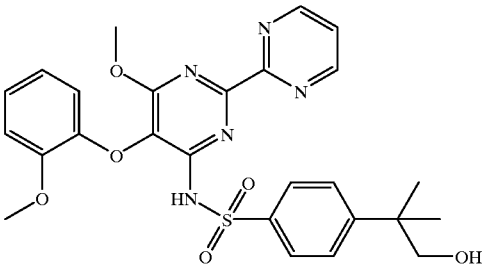

*Streptomyces rimosus* subsp. *rimosus* ATCC10970 maintained on a quarter strength ATCC172 agar slope was inoculated as a loopful of spores into a 300 ml Erlenmeyer flask containing 50 ml of AS-7H inoculum medium. This was allowed to incubate for 2 days at 28° C., 200 rpm on an Infors Multitron™ Shaker with 1" throw. 2 mls of this inoculum medium was then transferred to twenty 300 ml Erlenmeyer flask containing 50 ml of AP-5H production medium and incubated under the same conditions for a further 24 hours. At this point 15 mg of 4-tert-butyl-N-[6-methoxy-5-(2-methoxyphenoxy)-2-(2-pyrimidinyl)-4-pyrimidinyl]benzenesulfonamide (Preparation 7) dissolved in 0.5 ml of methanol was added to each of the flasks and the fermentation allowed to continue under the same conditions for a further 20 hours. The flask was then extracted with 200 mls of ethyl acetate and the combined ethyl acetate extracts concentrated to dryness to give a gum solid, 1100 mg.

The crude extract was purified by preparative reversed phase HPLC with a Phenomenex Magellen™ 5μ C18 column (150 mm×21.2 mm) in five injections. Using a gradient mobile phase of 90:10 to 40:60 water:acetonitrile from 3 to 20 minutes at a flow rate of 20 ml/min, the product was eluted at 19.0 minutes. The product fractions were concentrated under reduced pressure to yield the title compound as a colourless amorphous solid (84.4 mg).

HPLC retention time—Method A; 4.9 minutes.

$\delta_H$ (300 MHz, CDCl$_3$) 8.85 (1H, br s); 8.35 (2H, br s); 7.40 (3H, m); 7.10 (1H, m); 6.95 (2H, m); 6.80 (1H, m); 4.10 (3H, s); 3.95 (3H, s); 3.55 (2H, s); 1.80 (1H, br s); 1.30 (6H, s)

m/z (ESI, FTMS) [M+H]$^+$=538.1748, C$_{26}$H$_{28}$N$_5$O$_6$S requires 538.1755 m/z (ESI, FTMS) [M+Na]$^+$=560.1585, C$_{26}$H$_{27}$N5O$_6$SNa requires 560.1574

$\nu_{max}$ (PE) 3396, 2964, 1580, 1560, 1501, 1389, 1253, 1169, 1083, 865

EXAMPLE 10

Preparation and Isolation of N-[3-(2-ethoxyethoxy)-1-methyl-4-(4-methylphenyl)-1H-pyrazol-5-yl]-4-(2-hydroxy-1,1-dimethylethyl)benzenesulfonamide

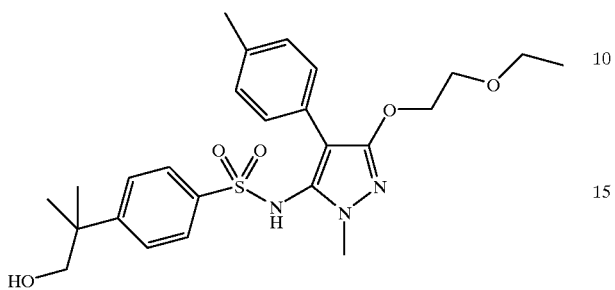

*Amycolata autotrophica* ATCC35203 maintained on a quarter strength ATCC172 agar slope was inoculated as a loopful of spores into five 300 ml Erlenmeyer flasks each containing 50 ml of MY inoculum medium. This was allowed to incubate for 2 days at 28° C., 200 rpm on an Infors Multitron™ Shaker with 1" throw. Two mls of this inoculum was then transferred to each of sixty 300 ml Erlenmeyer flask containing 50 ml of MY production medium and incubated under the same conditions for a further 24 hours. At this point 20 mg of 4-(tert-butyl)-N-[3-(2-ethoxyethoxy)-1-methyl-4-(4-methylphenyl)-1H-pyrazol-5-yl]benzenesulfonamide (Preparation 8) dissolved in 0.5 ml of methanol was added to each of the flasks and the fermentation allowed to continue under the same conditions for a further 6 hours. Each flask was then extracted with 200 mls of ethyl acetate and the combined ethyl acetate solubles concentrated to dryness to give a gum solid, 2.0 g.

The crude extract was purified by preparative reversed phase HPLC with a Phenomenex Magellen™ 5μ C18 column (150 mm×21.2 mm) in five injections. Using a gradient mobile phase of 35:65 to 20:80 water:methanol from 1.5 to 20 minutes at a flow rate of 20 ml/min, the product was eluted at 9.1 minutes. The product fractions were concentrated under reduced pressure to yield the title compound as a colourless amorphous solid (3.0 mg).

HPLC retention time—Method A; 10 minutes.

$\delta_H$ (300 MHz, CDCl$_3$) 7.40 (2H, d), 7.15 (2H, d); 6.90 (4H, m); 4.35 (2H, m); 3.85 (3H, s); 3.85 (2H, m); 3.55 (2H, q); 3.50 (2H, s); 2.25 (3H, s); 1.25 (6H, s) 1.20 (3H, t)

m/z (ESI) [M+H]$^+$=488.2218, C$_{25}$H$_{34}$N$_3$O$_5$S requires 488.2219 m/z (ESI) [M+Na]$^{30}$ =510.2026, C$_{25}$H$_{33}$N$_3$O$_5$SNa requires 510.2039

$\nu_{max}$ (PE) 3352, 2920, 1572, 1519, 1428, 1328, 1167

EXAMPLE 11

Preparation of N-(4-(1,3-benzodioxol-5-yl)-3-{2-[(5-chloro-2-pyrimidinyl)oxy]ethoxy}-1-methyl-1H-pyrazol-5-yl)-4-(2-hydroxy-1,1-dimethylethyl)benzenesulfonamide

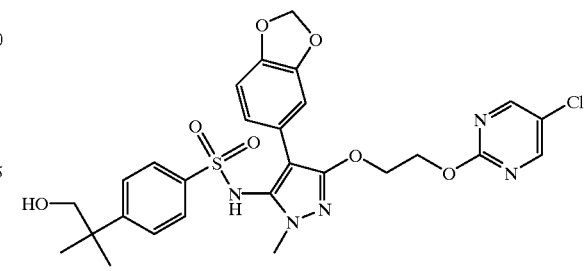

*Amycolata autotrophica* ATCC35203 maintained on a quarter strength ATCC172 agar slope was inoculated as a loopful of spores into a 300 ml Erlenmeyer flasks each containing 50 ml of MY inoculum medium. This was allowed to incubate for 2 days at 28° C., 200 rpm on an Infors Multitron™ Shaker with 1" throw. Two mls of this inoculum was then transferred to each of nine 300 ml Erlenmeyer flask containing 50 ml of MY production medium and incubated under the same conditions for a further 24 hours. At this point 5 mg of N-(4-(1,3-benzodioxol-5-yl)-3-{2-[(5-chloro-2-pyrimidinyl)oxy]ethoxy}-1-methyl-1H-pyrazol-5-yl)4-(tert-butyl)benzenesulfonamide (GB Patent Application No 9917858.4) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed. phase HPLC with a Phenomenex Magellen™ 5μ C18 column (150 mm×21.2 mm) in seven injections. Using a gradient mobile phase of 35:65 to 20:80 water:methanol from 1.5 to 20 minutes at a flow rate of 20 ml/min, the product was eluted at 8.4 minutes. The product fractions were concentrated under reduced pressure to yield the title compound as a colourless amorphous solid (10.0 mg).

HPLC retention time—Method A; 8 minutes.

$\delta_H$ (300 MHz, CDCl$_3$) 8.40 (2H, s); 7.40 (2H, d); 7.20 (2H, d); 6.45 (2H, s); 6.40 (1H, s); 5.85 (2H, s); 4.70 (2H, m); 4.50 (2H, m); 3.85 (3H, s); 3.55 (2H, s); 1.25 (6H, s)

m/z (ESI) [M+H]$^+$=602.1474, C$_{27}$H$_{29}$ClN$_5$O$_7$S requires 602.1476 m/z (ESI) [M+Na]$^+$=624.1273, C$_{27}$H$_{29}$ClN$_5$O$_7$SNa requires 624.1296

$\nu_{max}$ (NaCl) 3384, 2964, 1580, 1551, 1486, 1428, 1325, 1231, 1163, 1107, 1041, 936

EXAMPLE 12

Preparation of N-[4-(1,3-benzodioxol-5-yl)-3-(2-hydroxyethoxy)-1-methyl-1H-pyrazol-5-yl]-4-(2-hydroxy-1,1-dimethylethyl)benzenesulfonamide

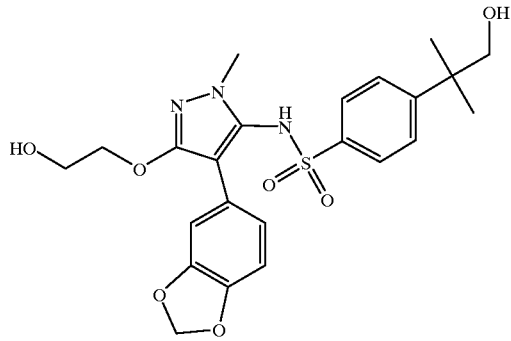

*Amycolata autotrophica* ATCC35203 maintained on a quarter strength ATCC172 agar slope was inoculated as a loopful of spores into a 300 ml Erlenmeyer flasks each containing 50 ml of MY inoculum medium. This was allowed to incubate for 2 days at 28° C., 200 rpm on an Infors Multitron™ Shaker with 1" throw. Two mls of this inoculum was then transferred to each of twenty 300 ml Erlenmeyer flask containing 50 ml of MY production medium and incubated under the same conditions for a further 24 hours. At this point 5 mg of N-[4-(1,3-benzodioxol-5-yl)-3-(2-hydroxyethoxy)-1-methyl-1H-pyrazol-5-yl]-4-(tert-butyl)benzenesulfonamide (GB Patent Application No 9917858.4) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in two injections. Using a gradient mobile phase of 85:15 to 15:85 water:methanol from 0 to 25 minutes at a flow rate of 20 ml/min, the product was eluted at 14.4 minutes. The product fractions were concentrated under reduced pressure to yield the title compound as a colourless amorphous solid (19.8 mg).

HPLC retention time—Method A; 3.8 minutes.

$\delta_H$ (300 MHz, CD$_3$OD) 7.45 (2H, d); 7.20 (2H, d); 6.80 (1H, s); 6.75 (1H, d); 6.45 (1H, d); 5.85 (2H, s); 4.20 (2H, m); 3.80.(2H, m); 3.70 (3H, s); 3.45 (2H, s); 1.25 (6H, s)

m/z (ESI) [M+H]$^+$=490.1669, C$_{23}$H$_{28}$N$_3$O$_7$S requires 490.1648 m/z (ESI) [M+Na]$^+$=512, 1467, C$_{23}$H$_{27}$N$_3$O$_7$SNa requires 512.1467

$\nu_{max}$ (PE) 3310, 2923, 1596, 1502, 1336, 1231, 1164, 1106, 1040, 934

EXAMPLE 13

Preparation of N-(4-(1,3-benzodioxol-5-yl)-3-{2-[(5-chloro-2-pyrimidinyl)oxy]ethoxy}-1-methyl-1H-pyrazol-5-yl)-5-(2-hydroxy-1-methylethyl)-2-pyridinesulfonamide

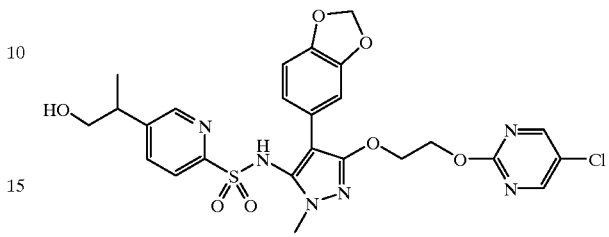

*Streptomyces rimosus* subsp. *rimosus* ATCC10970 maintained on a quarter strength ATCC172 agar slope was inoculated as a loopful of spores into a 300 ml Erlenmeyer flask containing 50 ml of AS-7H inoculum medium. This was allowed to incubate for 2 days at 28° C., 200 rpm on an Infors Multitron™ Shaker with 1" throw. 2 mls of this inoculum medium was then transferred to each of twenty 300 ml Erlenmeyer flask containing 50 ml of AP-5H production medium and incubated under the same conditions for a further 24 hours. At this point 5 mg of N-(4-(1,3-benzodioxol-5-yl)-3-{-2-[(5-chloro-2-pyrimidinyl)oxy]ethoxy}-1-methyl-1H-pyrazol-5-yl)-5-isopropyl-2-pyridinesulfonamide (Preparation 12) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in one injection. Using a gradient mobile phase of 85:15 to 15:85 water/methanol from 0 to 25 minutes at a flow rate of 20 ml/min, the product was eluted at 16.0 minutes. The fractions containing product were further purified using a Phenomenex Lichrosphere™ 5μ DIOL column (250 mm×21.2 mm) in one injection. Using an isocratic mobile phase of 40:60 isopropanol:dichloromethane, the product was eluted at 7.2 minutes. The product fractions were concentrated under reduced pressure to yield the title compound as a colourless amorphous solid (8.4 mg).

HPLC retention time—Method A; 5.5 minutes.

$\delta_H$ (400 MHz, CD$_3$OD) 8.50 (2H, s); 8.20 (1H, s); 7.55 (2H, m); 6.60 (2H, m); 6.45 (1H, d); 5.85 (2H, s); 4.70 (2H, m); 4.50 (2H, m); 3.75 (3H, s); 3.55 (2H, d); 2.85 (1H, m); 1.15 (3H, d)

m/z (ESI) [M+H]$^+$=589.1267, C$_{25}$H$_{26}$ClN$_6$O$_7$S requires 589.1272 m/z (ESI) [M+Na]$^+$=611.1101, C$_{25}$H$_{25}$ClN$_6$O$_7$SNa requires 611.1092

$\nu_{max}$ (PE) 3239, 2949, 1580, 1427, 1326, 1232, 1176, 1041

EXAMPLE 14

Preparation of 2-[4-({[3-(2-methoxyethoxy)-1-methyl-4-(4-methylphenyl)-1H-pyrazol-5-yl]amino}sulfonyl)phenyl]-2-methylpropanoic acid

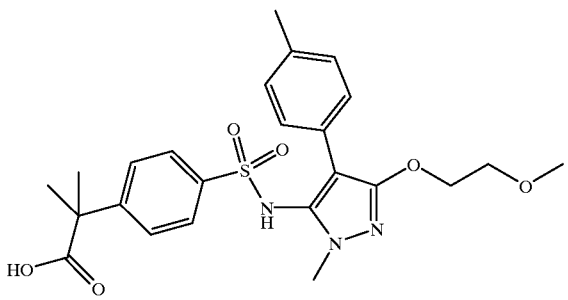

*Amycolata autotrophica* ATCC35203 maintained on a quarter strength ATCC172 agar slope was inoculated as a loopful of spores into a 300 ml Erlenmeyer flasks each containing 50 ml of MY inoculum medium. This was allowed to incubate for 2 days at 28° C., 200 rpm on an Infors Multitron™ Shaker with 1" throw. Two mls of this inoculum was then transferred to each of six 300 ml Erlenmeyer flask containing 50 ml of MY production medium and incubated under the same conditions for a further 24 hours. At this point 5 mg of 4-(tert-butyl)-N-[3-(2-methoxyethoxy)-1-methyl-4-(4-methylphenyl)-1H-pyrazol-5-yl]benzenesulfonamide (Preparation 17) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μC18 column (150 mm×21.2 mm) in one injection. Using a gradient mobile phase of 85:15 to 15:85 water:methanol from 0 to 25 minutes at a flow rate of 20 ml/min, the product was eluted at 17.0 minutes. The product fractions were concentrated under reduced pressure to yield the title compound as a colourless amorphous solid (4.0 mg).

HPLC retention time—Method A; 7.4 minutes.

$\delta_H$ (300 MHz, CDCl$_3$:CD$_3$OD 3:1) 7.30 (4H, m); 7.05 (2H, d); 6.80 (2H, d); 4.15 (2H, m); 3.60 (2H, m); 3.35 (3H, s); 3.30 (3H, s); 2.15 (3H, s); 1.35 (6H, s)

m/z (ESI, FTMS) [M+H]$^+$=488.1833, C$_{24}$H$_{30}$N$_3$O$_6$S requires 488.1850

$\nu_{max}$ (PE) 3373, 2968, 1564, 1483, 1399, 1358, 1171, 1134, 1099

EXAMPLE 15

Preparation of 2-[4-({[3-(2-ethoxyethoxy)-1-methyl-4-(4-methylphenyl)-1H-pyrazol-5-yl]amino}sulfonyl)phenyl]-2-methylpropanoic acid

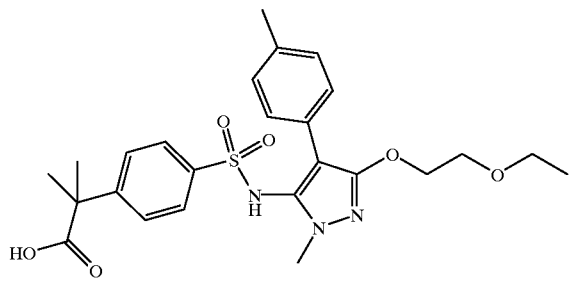

*Amycolata autotrophica* ATCC35203 maintained on a quarter strength ATCC172 agar slope was inoculated as a loopful of spores into a 300 ml Erlenmeyer flasks each containing 50 ml of MY inoculum medium. This was allowed to incubate for 2 days at 28° C., 200 rpm on an Infors Multitron™ Shaker with 1" throw. Two mls of this inoculum was then transferred to each of six 300 ml Erlenmeyer flask containing 50 mm of MY production medium and incubated under the same conditions for a further 24 hours. At this point 5 mg of 4-(tert-butyl)-N-[3-(2-ethoxyethoxy)-1-methyl-4-(4-methylphenyl)-1H-pyrazol-5-yl]benzenesulfonamide (Preparation 8) dissolved in 0.5 ml of methanol was added to each of the flasks and the fermentation allowed to continue under the same conditions for a further 96 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in one injection. Using a gradient mobile phase of 85:15 to 15:85 water:methanol from 0 to 25 minutes at a flow rate of 20 ml/min, the product was eluted at 16.5 minutes. The product fractions were concentrated under reduced pressure to yield the title compound as a colourless amorphous solid (1.5 mg).

HPLC retention time—Method A; 9.3 minutes.

$\delta_H$ (300 MHz, CDCl$_3$:CD$_3$OD 3:1) 7.30 (4H, m); 7.05 (2H, d); 6.75 (2H, d); 4.10 (2H, m); 3.60 (2H, m); 3.45 (2H, q); 3.35 (3H, s); 2.10 (3H, s); 1.30 (6H, s); 1.05 (3H, t)

m/z (ESI, FTMS) [M+H]$^+$=502.1995, C$_{25}$H$_{32}$N$_3$O$_6$S requires 502.2006 m/z (ESI, FTMS) [M+Na]$^+$=524.1811, C$_{25}$H$_{31}$N$_3$O$_6$SNa requires 524.1825

EXAMPLE 16

Preparation of N-(4-(1,3-benzodioxol-5-yl)-3-{2-[(5-bromo-2-pyrimidinyl)oxy]ethoxy}-5-isoxazolyl)-4-(2-hydroxy-1,1-dimethylethyl)benzenesulfonamide

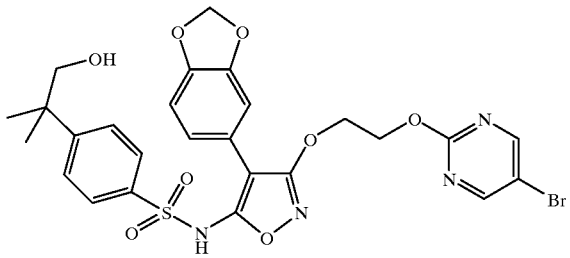

*Amycolata autotrophica* ATCC35203 maintained on a quarter strength ATCC172 agar slope was inoculated as a loopful of spores into a 300 ml Erlenmeyer flasks each containing 50 ml of of MY inoculum medium. This was allowed to incubate for 2 days at 28° C., 200 rpm on an Infors Multitron™ Shaker with 1" throw. Two mls of this inoculum was then transferred to each of twenty 300 ml Erlenmeyer flask containing 50 ml of MY production medium and incubated under the same conditions for a further 24 hours. At this point 5 mg of N-(4-(1,3-benzodioxol-5-yl)-3-{2-[(5-bromo-2-pyrimidinyl)oxy]ethoxy}-5-isoxazolyl)-4-(tert-butyl)benzenesulfonamide (Preparation 20) dissolved in 0.5 ml of methanol was added to each of the flasks and the fermentation allowed to continue under the same conditions for a further 144 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5μ C18 column (150 mm×21.2 mm) in two injections. Using a gradient mobile phase of 35:65 to 20:80 water:methanol from 1.5 to 29 minutes at a flow rate of 20 ml/min, the product was eluted at 4.1 minutes. The product fractions were purified again on the same column in one injection. Using a gradient mobile phase of 85% to 15% water/methanol from 0 to 25 minutes at a flow rate of 20 ml/min, the product was eluted at 14.9 minutes. The product fractions were concentrated under reduced pressure to yield the title compound as a colourless amorphous solid (2.0 mg).

HPLC retention time—Method A; 8.6 minutes.

$\delta_H$ (300 MHz, CDCl$_3$) 8.40 (2H, s); 7.70 (2H, d); 7.10 (2H, d); 7.05 (2H, m); 6.55 (1H, d); 5.75 (2H, s); 4.55 (2H, m); 4.40 (2H, m); 3.35 (2H, s); 1.05 (6H, s)

m/z (ESI) [M+H]$^+$=633.0655, C$_{26}$H$_{26}$BrN$_4$O$_8$S requires 633.0655 m/z (ESI) [M+Na]$^+$=655.0481, C$_{26}$H$_{25}$BrN$_4$O$_8$SNa requires 655.0474

$\nu_{max}$ (PE) 3373, 2968, 1564, 1483, 1399, 1358, 1171, 1134, 1099

PREPARATIONS

Preparation 1

Preparation of N-[6-methoxy-5-(2-methoxyphenoxy)-2-(2-pyrimidinyl)-4-pyrimidinyl]-3,3-dimethyl-1-butanesulfonamide Sodium hydride (80% oil dispersion 132 mg) was cautiously added to a suspension of N-[6-chloro-5-(2-methoxyphenoxy)-2-(2-pyrimidinyl)-4-pyrimidinyl]-3,3-dimethyl-1-butanesulfonamide (Preparation 2)(420 mg) in dry methanol (12 ml) divided equally between two 10 ml Wheaton reacti-vials™, and the resulting mixtures stirred at 100° C. for 3 hours. The reactions were then combined and partitioned between ethyl acetate (40 ml) and 2N aqueous hydrochloric acid (20 ml) and the organic phase separated. The aqueous was extracted with ethyl acetate (20 ml) and the organic phases combined, washed (water 2×20 ml), dried (Na$_2$SO$_4$) and evaporated under reduced pressure. Column chromatography on silica eluting with a solvent gradient of dichloromethane:methanol 99:1 changing to 97:3 gave N-[6-methoxy-5-(2-methoxyphenoxy)-2-(2-pyrimidinyl)-4-pyrimidinyl]-3,3-dimethyl-1-butanesulfonamide as an off-white coloured foam (265 mg).

$\delta_H$ (400 MHz, d$_6$DMSO+2 dps TFA-D) 8.95 (2H, m); 7.60 (1H, m); 7.10 (1H, d); 7.00 (1H, t); 6.80 (1H, t); 6.65 (1H, d); 3.90 (2H, m); 3.90 (3H, s); 3.80 (3H, s); 1.60 (2H, m); 0.85 (9H, s)

m/z (TSPI) [M+H]$^+$=474.0, C$_{22}$H$_{28}$N$_5$O$_5$S requires 474.2

Analysis: Found C, 51.32; H, 5.51; N, 13.17. C$_{22}$H$_{27}$N$_5$O$_5$S.0.6 CH$_2$Cl$_2$ requires C, 51.75; H, 5.42; N, 13.35.

Preparation 2

Preparation of N-[6-chloro-5-(2-methoxyphenoxy)-2-(2-pyrimidinyl)-4-pyrimidinyl]-3,3-dimethyl-1-butanesulfonamide Potassium tert-butoxide (340 mg) was added to 3,3-dimethylbutane-1-sulphonic acid amide (J.Org. Chem., 1956, 21, 385) (500 mg) in dry tetrahydrofuran (10 ml) at room temperature under nitrogen. The resulting mixture was stirred for 1 hour and then concentrated under reduced pressure. The residual potassium salt was re-evaporated from dry toluene, oven dried at 40° C. under vacuum, and used directly.

3,3-dimethylbutane-1-sulphonic acid amide potassium salt (616 mg) was added to a solution of 4,6-dichloro-5-(2-methoxyphenoxy)-2-(pyrimidin-2-yl)-pyrimidine (Can. Pat. Appl. 2071193) (353 mg) in dry dimethyl sulphoxide (10 ml) and the resulting mixture stirred at 120° C. for 6 hours under nitrogen. The reaction mixture was allowed to cool and then partitioned between ethyl acetate (30 ml) and 2N aqueous hydrochloric acid (30 ml) and the organic phase separated. The aqueous was extracted with ethyl acetate (30 ml) and the organic phases combined, washed (water 2×20 ml), dried (Na$_2$SO$_4$) and evaporated under reduced pressure. Column chromatography on silica eluting with a solvent gradient of pentane:ethyl acetate 50:50 changing to 0:100 and finally ethyl acetate:methanol 98:2 gave N-[6-chloro-5-(2-methoxyphenoxy)-2-(2-pyrimidinyl)-4-pyrimidinyl]-3,3-dimethyl-1-butanesulfonamide as an off-white solid (440 mg).

$\delta_H$ (300 MHz, d$_6$DMSO) 9.00 (2H, d); 7.65 (1H, t); 7.10 (2H, m); 6.85 (2H, m); 6.75 (1H, bs); 3.95 (2H, m); 3.80 (3H, s); 1.55 (2H, m); 0.95 (9H, s)

m/z (TSPI) [M+H]$^+$=478.0, C$_2$H$_{25}$ClN$_5$O$_4$S requires 478.1

Preparation 3

Preparation of N-[6-methoxy-5-(2-methoxyphenoxy)-2-(2-pyrimidinyl)-4-pyrimidinyl]-4,4-dimethyl-1-pentanesulfonamide Sodium hydride (60% oil dispersion 354 mg) was cautiously added to a suspension of N-[6-chloro-5-(2- methoxyphenoxy)-2-(2-pyrimidinyl)-4-pyrimidinyl]-4,4-dimethyl-1-pentanesulfonamide (580 mg) in dry methanol (5 ml) in a 10 mm Wheaton reacti-vial™ and the resulting mixture stirred at 105° C. for 4 hours. The reaction was then partitioned between ethyl acetate (20 ml) and 2N aqueous hydrochloric acid (10 ml) and the organic phase separated. The aqueous was extracted with ethyl acetate (20 ml ) and the organic phases combined, washed (water 2×20 ml), dried ($Na_2SO_4$) and evaporated under reduced pressure. Column chromatography on silica eluting with a solvent gradient of dichloromethane:methanol 100:0 changing to 98.5:1.5 gave N-[6-methoxy-5-(2-methoxyphenoxy)-2-(2-pyrimidinyl)-4-pyrimidinyl]-4,4-dimethyl-1-pentanesulfonamide as an off-white coloured solid (189 mg).

$\delta_H$ (400 MHz, $CDCl_3$) 8.95 (2H, d); 8.40 (1H, br s); 7.35 (1H, t); 7.10 (2H, m); 7.00 (1H, d); 6.90 (1H, t); 4.15 (3H, s); 4.00 (3H, s); 3.85 (2H, t); 1.85 (2H, m); 1.30 (2H, m); 0.85 (9H, s)

m/z (TSPI) $[M+H]^+$=488.0, $C_{23}H_{30}N_5O_5S$ requires 488.2

Analysis: Found C, 55.84; H, 6.01; N, 14.06. $C_{23}H_{29}N_5O_5S.0.5 H_2O$ requires C, 55.63; H, 6.09; N, 14.10.

Preparation 4

Preparation of N-[6-chloro-5-(2-methoxyphenoxy)-2-(2-pyrimidinyl)-4-pyrimidinyl]-4,4-dimethyl-1-pentanesulfonamide Caesium carbonate (2.62 g) was added to a solution of 4,4-dimethylpentane-1-sulphonic acid amide (720 mg) and 4,6-dichloro-5-(2-methoxyphenoxy)-2-(pyrimidin-2-yl)-pyrimidine (Can. Pat. Appl. 2071193) (1.40 g) in dry N,N-dimethyl formamide (8 ml) and the resulting mixture stirred at 80° C. for 4 hours under nitrogen. The reaction mixture was allowed to cool and then partitioned between ethyl acetate (40 ml) and 2N aqueous hydrochloric acid (20 ml). The organic phase was separated, washed (brine 2×20 ml), dried ($Na_2SO_4$) and evaporated under reduced pressure. Column chromatography on silica eluting with a solvent gradient of dichloromethane:methanol 100:0 changing to 99:1 gave crude product which was recrystallised from ethyl acetate:pentane to give N-[6-chloro-5-(2-methoxyphenoxy)-2-(2-pyrimidinyl)-4-pyrimidinyl]-4,4-dimethyl-1-pentanesulfonamide as a white solid (1.08 g).

$\delta_H$ (400 MHz, $CDCl_3$) 8.95 (2H, d); 8.55 (1H, brs); 7.40 (1H, t); 7.20 (1H, t); 7.10 (1H, d); 7.05 (1H, d); 6.95 (1H, t); 3.95 (3H, s); 3.90 (2H, m); 1.85 (2H, m); 1.30 (2H, m); 0.85 (9H, s)

m/z (TSPI) $[M+H]^+$=492.0, $C_{22}H_{26}ClN_5O_4S$

Preparation 5

Preparation of 4,4-dimethylpentane sulphonic acid amide

Anhydrous ammonia gas was passed into a solution of 4,4-dimethylpentane sulphonyl chloride (1.85 g) in dry tetrahydrofuran (5 ml) at 5–10° C. until saturation. The resulting suspension was stirred at room temperature for 18 hours and then evaporated under reduced pressure. The residue was partitioned between ethyl acetate (20 ml) and 2N aqueous hydrochloric acid (20 ml). The organic phase was separated, washed (brine 20 ml), dried ($Na_2SO_4$) and evaporated. Column chromatography on silica eluting with dichloromethane:methanol 98:2 gave 4,4-dimethylpentane sulphonic acid amide as an off-white solid (0.72 g).

$\delta_H$ (400 MHz, $CDCl_3$) 4.50 (2H, br s); 3.05 (2H, t); 1.85 (2H, m); 1.30 (2H, t); 0.90 (9H, s)

m/z (TSPI) $[M+NH_4]^+$=197.1, $C_7H_{21}N_2O_2S$ requires 197.1

Preparation 6

Preparation of 4,4-dimethylpentane sulphonyl chloride

Sodium sulphite (5.35 g) was added to a solution of 1-bromo-4,4-dimethylpentane (DE 2040784) (1.9 g) in a mixture of dioxan (15 ml) and water (15 ml). The resulting mixture was stirred at reflux for 15 hours and then evaporated under reduced pressure. The residue was triturated with toluene (2×30 ml), re-evaporated from toluene (2×30 ml) and then suspended in thionyl chloride (10 ml) and 2 drops of N,N-dimethylformamide added. The mixture was stirred at reflux for 1 hour, then allowed to cool and evaporated under reduced pressure. The residue was re-evaporated from toluene (25 ml) and then partitioned between ethyl acetate (25 ml) and 2N aqueous hydrochloric acid (25 ml). The organic phase was separated, washed (brine 25 ml), dried ($Na_2SO_4$) and evaporated to yield 4,4-dimethylpentane sulphonyl chloride as an orange/brown coloured oil (1.9 g).

$\delta_H$ (400 MHz, $CDCl_3$) 3.60 (2H, t); 2.00 (2H, m); 1.30 (2H, m); 0.90 (9H, s)

Preparation 7

Preparation of 4-tert-butyl-N-[6-methoxy-5-(2-methoxyphenoxy)-2-(2-pyrimidinyl)-4-pyrimidinyl] benzenesulfonamide 4-tert-Butyl-benzene sulphonyl chloride (286 mg) was added to a stirred solution of 4-amino-6-methoxy-5-(2-methoxyphenoxy)-2-(2-pyrimidinyl)-pyrimidine (EP 713875A1) (100 mg) in dry pyridine (2 ml) at room temperature and the resulting mixture stirred for 36 hours. The reaction was then partitioned between ethyl acetate (20 ml) and 2N aqueous hydrochloric acid (10 ml) and the organic phase separated, washed (2N aqueous hydrochloric acid 2×10 ml, water 2×10 ml), dried ($MgSO_4$) and evaporated under reduced pressure. Column chromatography on silica eluting with a solvent gradient of pentane:ethyl acetate 25:75 changing to 0:100, then dichloromethane:methanol 95:5 gave 4-tert-butyl-N-[6-methoxy-5-(2-methoxyphenoxy)-2-(2-pyrimidinyl)-4-pyrimidinyl] benzenesulfonamide as an off-white coloured solid (5 mg).

$\delta_H$ (400 MHz, $CDCl_3$) 9.00 (2H, d); 8.70 (1H, br s); 8.35 (2H, d); 7.40 (3H, m); 7.10 (1H, t); 7.00 (2H, d); 6.85 (1H, t); 4.10 (3H, s); 4.00 (3H, s); 1.25 (9H, s)

m/z (ESI, FTMS) $[M+H]^+$=522.1798, $C_{26}H_{27}N_5O_5S$ requires 522.1806

Preparation 8

Preparation of 4-(tert-butyl)-N-[3-(2-ethoxyethoxy)-1-methyl-4-(4-methylphenyl)-1H-pyrazol-5-yl)benzenesulfonamide

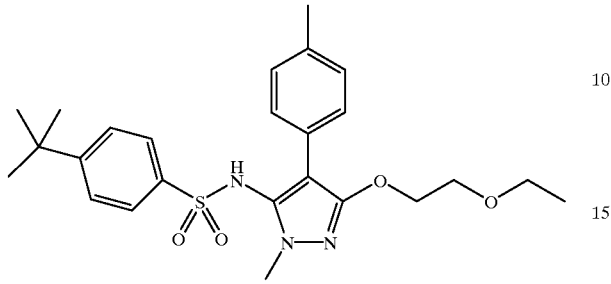

The method employed for Preparation 17 was used to prepare the title compound from 4-(tert-butyl)-N-{[4-(tert-butyl)phenyl]sulfonyl}-N-[3-(2-ethoxyethoxy)-1-methyl-4-(4-methylphenyl)-1H-pyrazol-5-yl]benzenesulfonamide (Preparation 9).

$\delta_H$ (400 MHz, CDCl$_3$) 7.36 (2H, d), 7.12 (2H, d), 6.85 (2H, d), 6.80 (2H, d), 6.58 (1H, s), 4.32 (2H, m), 3.83 (3H, s), 3.72 (2H, m), 3.52 (2H, q), 2.23 (3H, s), 1.24 (9H, s); 1.89 (3H, s).

m/z (ESI) [MH$^+$]=472.0, C$_{25}$H$_{34}$N$_3$O$_4$S requires 472.1

Preparation 9

Preparation of 4-(tert-butyl)-N-{[4-(tert-butyl)phenyl]sulfonyl}-N-[3-(2-ethoxyethoxy)-1-methyl-4-(4-methylphenyl)-1H-pyrazol-5-yl]benzenesulfonamide

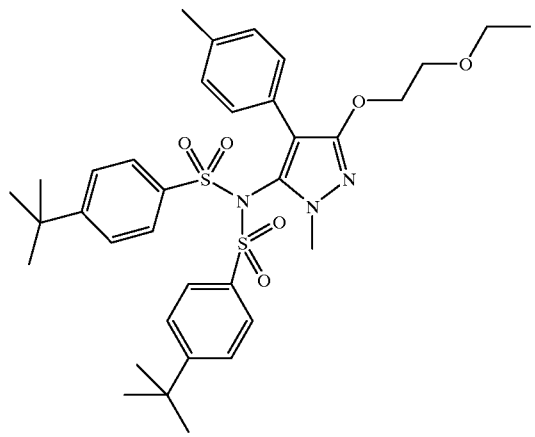

The method of Preparation 18 was used to prepare the title compound from 3-(2-ethoxyethoxy)-1-methyl-4-(4-methylphenyl)-1H-pyrazol-5-ylamine (Preparation 10)

$\delta_H$ (400 MHz, CDCl$_3$) 7.80 (4H, d), 7.40 (6H, m), 6.85 (2H, d), 4.40 (2H, m), 3.75 (2H, m), 3.40 (2H, q), 3.15 (3H, s), 2.25 (3H, s), 1.35 (18H, s), 1.25 (3H, t).

m/z (TSPI) [MH$^+$]=668.0, C$_{35}$H$_{46}$N$_5$S$_2$O$_6$ requires 668.1

Preparation 10

Preparation of 3-(2-ethoxyethoxy)-1-methyl-4-(4-methylphenyl)-1H-pyrazol-5-ylamine

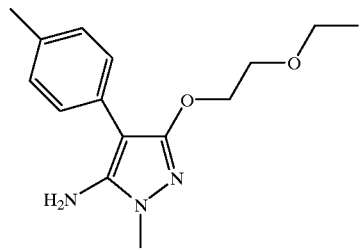

The method of Preparation 19 was used to prepare the title compound from 5-amino-1-methyl-4-(4-methylphenyl)-1H-pyrazol-3-ol (Preparation 11).

$\delta_H$ (400 MHz, CDCl$_3$) 7.35 (2H, d), 7.20 (2H, d), 4.35 (2H, m), 3.70 (2H, m), 3.65 (2H, s), 3.55 (5H, m), 2.35 (3H, s), 1.20 (3H, t).

m/z (TSPI) [MH$^+$]=276.0, C$_{15}$H$_{22}$N$_3$O$_2$ requires 276.1

Preparation 11

Preparation of 5-amino-1-methyl-4-(4-methylphenyl)-1H-pyrazol-3-ol

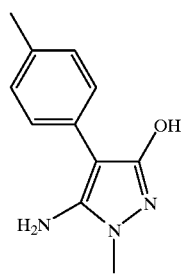

To ethyl (4-methylphenyl)cyanoacetate (Synthesis, 1985, 5, 506) (22.5 g) in ethanol (150 ml) at room temperature was added methylhydrazine (8.8 ml) dropwise over 30 minutes the mixture was heated to reflux temperature for 20 hrs. The reaction was evaporated to dryness. The residue was recrystalised in ethanol to yield the title compound as a white solid (8.3 g).

$\delta_H$ (300 MHz, d$_6$DMSO) 9.40 (1H, br. s), 7.40 (2H, d), 7.05 (2H, d), 5.60 (2H, br. s), 3.10 (3H, s), 2.25 (3H, s).

m/z (TSPI) [MH$^+$]=204.2, C$_{11}$H$_{14}$N$_3$O requires 204.1

EXAMPLE 12

Preparation of N-(4-(1,3-benzodioxol-5-yl)-3-{2-[(5-chloro-2-pyrimidinyl)oxy]ethoxy-}1-methyl-1H-pyrazol-5-yl)-5-isopropyl-2-pyridinesulfonamide

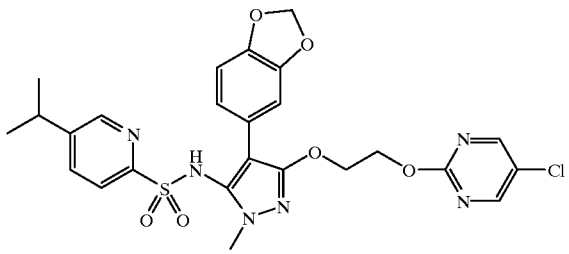

In an oven-dried flask a solution of tetrahydrofuran (50 ml) and dimethylacetamide (3 ml) was treated with sodium hydride as a 60% dispersion in oil (460 mg) under an atmosphere of nitrogen. The reaction was stirred for 5 min and then treated with N-[4-(1,3-benzodioxol-5-yl)-3-(2-hydroxyethoxy)-1-methyl-1H-pyrazol-5-yl]-5-isopropyl-2-pyridinesulfonamide (1.0 g) (Preparation 13). The reaction was stirred for 3 h and was then treated with 5-chloro-2 (methylsulfonyl)pyrimidine (460 mg). After stirring for a further 3 h the reaction mixture was concentrated and the residue was partitioned between water (100 ml) and ethyl acetate (100 ml). The aqueous was extracted with ethyl acetate (3×75 ml) and the combined organics were dried over sodium sulfate. The solvent was removed and the crude residue was purified on a silica (40 g) column eluting with 20% ether in dichloromethane rising to 45% ether in dichloromethane to yield the title compound as an off-white foam (560 mg).

$\delta_H$ (400 MHz, CDCl$_3$) 1.25 (m, 6H), 2.90 (m, 1H), 3.80 (s, 3H), 4.55 (m, 2H), 4.70 (m, 2H), 5.85 (s, 2H), 6.50 (s, 3H), 7.45 (m, 1H), 7.55 (m, 1H), 8.20 (m, 1H), 8.40 (s, 2H)

m/z (TSPI) [MH$^+$]=573.5 C$_{25}$H$_{25}$N$_6$O$_6$ClS+H requires 573.1

Preparation 13

Preparation of N-[4-(1,3-benzodioxol-5-yl)-3-(2-hydroxyethoxy)-1-methyl-1H-pyrazol-5-yl]-5-isopropyl-2-pyridinesulfonamide

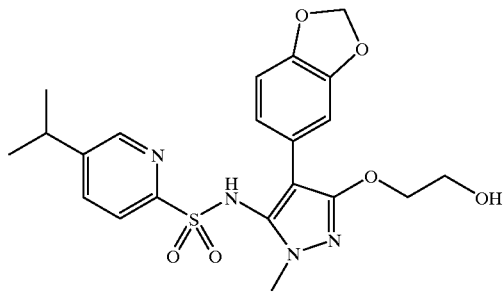

To a solution of 2-[(4-(1,3-benzodioxol-5-yl)-5{-bis[(5-isopropyl-2-pyridinyl)sulfonyl]amino}-1-methyl-1H-pyrazol-3-yl)oxy]ethyl acetate (Preparation 14) (9.0 g) in ethanol (200 ml) was added 2.0M aqueous sodium hydroxide (25 ml). The reaction was stirred for 30 min and concentrated under reduced pressure and the residue was poured onto 0.5M aqueous citric acid (300 ml). This was extracted with ethyl acetate (3×80 ml) and dried over magnesium sulfate. The solvent was removed under reduced pressure and the crude residue was purified by silica (230 g) chromatography eluting with a gradient of 50% ethyl acetate in hexane to 70% ethyl acetate in hexane to afford the title product as a white solid (5.0 g)

$\delta_H$ (400 MHZ, CDCl$_3$) 1.25 (6H, s), 2.90 (m, 1H), 3.80 (3H, s), 3.90 (2H, m), 4.30 (2H, m), 5.85 (2H, s), 6.55–6.60 (3H, m), 7.45 (1H, m), 7.60 (1H, m), 8.20 (1H, s)

m/z (TSPI) [MH$^+$]=461 C$_{21}$H$_{25}$N$_4$O$_6$S requires 461.1

Preparation 14

Preparation of 2-[(4-(1,3-benzodioxol-5-yl)-5-{bis[(5-isopropyl-2-pyridinyl)sulfonyl]amino}-1-methyl-1H-pyrazol-3-yl)oxy]ethyl acetate

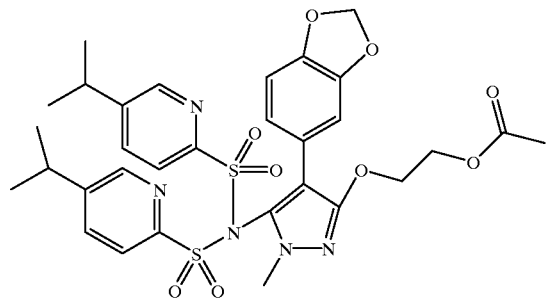

To a solution of 4-dimethylaminopyridine (6.17 g) in anhydrous pyridine (100 ml) under an atmosphere of nitrogen and at 0° C. was added 5-isopropyl-2-pyrindinylsulfonyl chloride (11.1 g). The reaction was then treated dropwise at 0° C. with a solution of 2-{[5-amino-4-(1,3-benzodioxol-5-yl)-1-methyl-1H-pyrazol-3-yl]oxy}ethyl acetate (Preparation 15) (10.8 g) in anhydrous pyridine (20 ml). The reaction was allowed to warm to room temperature and then stirred for 12 h. The reaction mixture was poured into 1.0M aqueous citric acid (500 ml) and extracted with ethyl acetate (3×200 ml). The combined organics were washed with brine (150 ml) and dried over magnesium sulfate. The solvent was removed under reduced pressure and the residue was purified on a silica (700 g) column using an eluent gradient of 30% ethyl acetate in hexane to 50% ethyl acetate in hexane to afford the title product as a white solid (9.5 g).

$\delta_H$ (400 MHz, CDCl$_3$) 1.30 (12H, s), 2.05 (3H, s), 3.05 (m, 2H), 3.95 (3H, s), 4.35–4.40 (4H, m), 5.85 (2H, s), 6.55 (1H, d), 6.95 (1H, d), 7.05 (1H, s), 7.65 (2H, d), 8.05 (2H, d), 8.40 (2H, s)

Preparation 15

Preparation of 2-{[5-amino-4-(1,3-benzodioxol-5-yl)-1-methyl-1H-pyrazol-3-yl]oxy}ethyl acetate

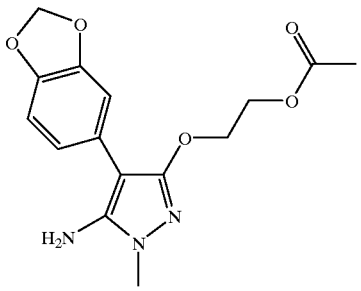

5-amino-4-(1,3-benzodioxol-5-yl)-1-methyl-1H-pyrazol-3-ol (Preparation 16) (11.39 g) was dissolved in dimethylformamide (40 mm), caesium carbonate (15.9 g) was added followed by 2-bromoethylacetate (8.16 g). The mixture was stirred at room temperature for 16 hours. The mixture was treated with water (750 ml) and extracted with ethyl acetate (2×250 ml). The organic fractions were combined washed with water (3×350 ml), brine (250 ml), dried over magnesium sulfate, filtered and evaporated. The crude product was purified on. silica (300 g) eluting with ethyl acetate:hexane (3:1) to yield the title compound as a white solid (5.57 g).

$\delta_H$ (300 MHz, CDCl$_3$) 6.95 (1H, s), 6.90 (2H, s), 5.95 (2H, s), 4.40 (4H, s) 3.60 (2H, s), 3.50 (3H, s), 2.05 (3H, s).

Preparation 16

Preparation of 5-amino-4-(1,3-benzodioxol-5-yl)-1-methyl-1H-pyrazol-3-ol

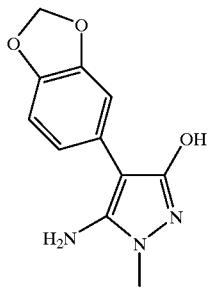

Methylhydrazine (6 ml) was added dropwise to a solution of ethyl 2-|(1,3-benzodioxol-5-yl)-2-cyanoacetate (20.0 g) in ethanol (100 ml) and the mixture was refluxed overnight. The solution was subsequently allowed to cool to room temperature. Concentration to dryness afforded a residue, which was triturated with hot ethanol. The residue was washed with cold ethanol and dried to afford the title compound as a white solid (15.0 g).

$\delta_H$ (400 MHz, CDCl$_3$) 9.45 (1H, br. s), 7.05 (1H, s), 6.90 (1H, d), 6.80 (1H, d), 5.90 (2H, s), 5.65 (2H, br), 3.15 (3 H, s).

m/z (TSPI) [MH$^+$]=234.1, C$_{11}$H$_{12}$N$_3$O$_3$ requires 234.1

Preparation 17

Preparation of 4-(tert-butyl)-N-[3-(2-methoxyethoxy)-1-methyl-4-(4-methylphenyl)-1H-pyrazol-5-yl)benzenesulfonamide

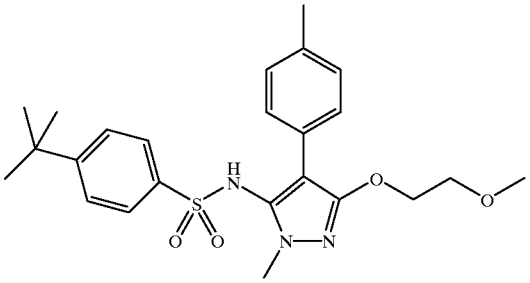

4-(tert-Butyl)-N-{[4-(tert-butyl)phenyl]sulfonyl}-N-[3-(2-methoxyethoxy)-1-methyl-4-(4-methylphenyl)-1H-pyrazol-5-yl]benzenesulfonamide (Preparation 18)(278 mg) was dissolved in dioxane, 1M sodium hydroxide solution (4 ml) was added and the reaction was stirred at reflux for 0.5 hours. The solvent was removed under reduced pressure. The residue was partitioned between ethyl acetate and 1M hydrochloric acid. The organic phase was separated, dried over magnesium sulphate and the solvent removed under reduced pressure. The product was purified on silica (10 g) eluting with a solvent gradient of pentane:ethyl acetate (1:0 to 6.4) to yield the title compound as a white solid (160 mg).

$\delta^H$ (400 MHz, CDCl$_3$) 7.36 (2H, d), 7.12 (2H, d), 6.85 (2H, d), 6.80 (2H, d), 6.55 (1H, s), 4.32 (2H, m), 3.85 (3H, s), 3.66 (2H, m), 3.35 (3H, s), 2.23 (3H, s), 1.24 (9H, s).

m/z (ESI) [MH$^+$]=458.0, C$_{24}$H$_{32}$N$_3$O$_4$S requires 457.1

Preparation 18

Preparation of 4-(tert-butyl)-N-{[4-(tert-butyl)phenyl]sulfonyl}-N-[3-(2-methoxyethoxy)-1-methyl-4-(4-methylphenyl)-1H-pyrazol-5-yl]benzenesulfonamide 5-Amino-3-(2-methoxyethoxy)-1-methyl-4-(4-methylphenyl)-1H-pyrazole (Preparation 19) (183 mg) was dissolved in dichloromethane (5 ml) and tert-butylbenzenesulfonyl chloride (652 mg), potassium hydroxide (550 mg) and tetra-n-butylammonium hydrogen sulfate (61 mg) were added sequentially. The reaction was sonicated for 3 hours. The solvent was removed under reduced pressure. The residue was dissolved in ethyl acetate (50 ml), washed with water (50 ml), dried over magnesium sulfate, filtered and evaporated. The residue was purified by column chromatography over silica (20 g) eluted with a gradient of pentane:ethyl acetate (1:0 to 1:1) to yield the title compound as a white solid (278 mg).

$\delta_H$ (400 MHz, CDCl$_3$) 7.80 (4H, d), 7.40 (6H, m), 6.90 (2H, d), 4.40 (2H, m), 3.70 (2H, m), 3.40 (3H, s), 3.20 (3H, s), 2.25 (3H, s), 1.35 (18H, s).

m/z (TSPI) [MH$^+$]=654.0, C$_{34}$H$_{44}$N$_3$S$_2$O$_6$ requires 654.1

Preparation 19

Preparation of 5-amino-3-(2-methoxyethoxy)-1-methyl-4-(4-methylphenyl)-1H-pyrazole

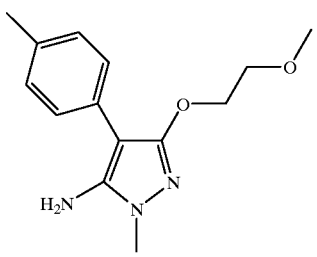

5-amino-1-methyl-4-(4-methylphenyl)-1H-pyrazol-3-ol (Preparation 11) (305 mg) was dissolved in dimethylformamide (2 ml), potassium carbonate (622 mg) and 2-bromoethyl methyl ether (208 mg) were added. The reaction was stirred at room temperature for 1.5 hours and then at 50° C. for 12 hours. The solvent was removed under reduced pressure. The crude product was purified on silica (10 g) eluted with a solvent gradient of pentane:ethyl acetate (1:0 to 0:1) to yield the title compound as a white solid (201 mg).

$\delta_H$ (400 MHz, CDCl$_3$) 7.35 (2H, d), 7.20 (2H, d), 4.35 (2H, m), 3.70 (2H, m), 3.65 (2H, s), 3.60 (3H, s), 3.40 (3H, s), 2.35 (3H, s).

m/z (TSPI) [MH$^+$]=262.0, C$_{14}$H$_{20}$N$_3$O$_2$ requires 262.1

Preparation 20

Preparation of N-(4-(1,3-benzodioxol-5-yl)-3-{2-[(5-bromo-2-pyrimidinyl)oxy]ethoxy}5-isoxazolyl)-4-(tert-butyl)benzenesulfonamide

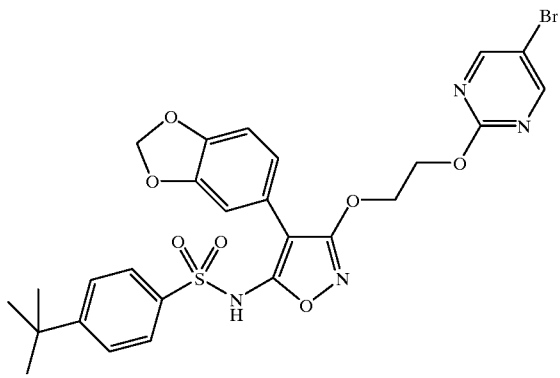

To a solution of N-[4-(1,3-benzodioxol-5-yl)-3-(2-hydroxyethoxy)-5-isoxazolyl]-4-(tert-butyl) benzenesulfonamide (Preparation 21) (90 mg) in tetrahydrofuran (1.5 ml), purged with nitrogen three times, was added sodium hydride (16 mg of a 60% dispersion in oil) and the reaction mixture stirred for 15 minutes. After which time a solution of 5-bromo-2-chloropyrimidine (41 mg) in tetrahydrofuran (0.5 ml) was added to the reaction followed by 4-dimethylacetamide (0.1 ml). The reaction mixture was left stirring at room temperature overnight. This solution was added to a stirring mixture of ether (30 ml) and citric acid (1.0M, 30 ml) The organics were separated and further washed with brine (30 ml) and dried over magnesium sulfate before being concentrated in vacuo to yield the crude material (90 mg). This was purified by HPLC on a 5$\mu$ ODS Phenomenex Magellen™ column with a isocratic elution of 0.1M NH40Ac (55%) and acetonitrile (45%) to yield the desired product as a white solid (10 mg).

$\delta_H$ (300 MHz, CDCl$_3$) 8.50(2H, s), 7.85(2H, d), 7.50(2H, d), 6.85(2H, d),6.75(1H, d), 5.95(2H, s), 4.75(2H, m), 4.65 (2H, m), 1.35(9H, s)

m/z (TSPI) [MH$^+$]=618.5, C$_{26}$H$_{26}$BrN$_4$O$_7$S requires 617.5

Preparation 21

Preparation of N-[4-(1,3-benzodioxol-5-yl)-3-(2-hydroxyethoxy)-5-isoxazolyl]-4-(tert-butyl)benzenesulfonamide

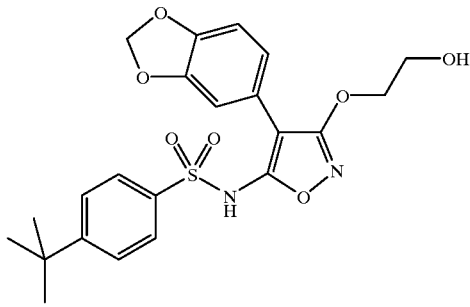

To a stirring solution of 2-({5-[{[4-(tert-butyl)phenyl] sulfonyl}(isobutoxycarbonyl)amino]-4-iodo-3-isoxazolyl}oxy)ethyl acetate (Preparation 22) (2.41 g) in dioxane (25 ml) was added (3,4-methylenedioxyphenyl) boronic acid (0.72 g) followed by cesium carbonate (5.15 g) and water (3 ml). The reaction mixture was purged with nitrogen three times, after which time tetrakis (triphenylphosphine)palladium(0) (140 mg). The reaction mixture was heated to reflux for about 2 hours. Ethanol (50 ml) and sodium hydroxide (2M, 50 ml) were added to the reaction mixture and then this was stirred at room temperature overnight. The reaction mixture was concentrated in vacuo and the solid residue was partitioned between saturated ammonium chloride solution (100 ml) and ethyl acetate (100 ml). The organics were washed with brine (50 ml), dried over sodium sulfate and concentrated under reduced pressure to yield the crude material as a brown oil. The crude material was purified by column chromatography (100 g silica, crude loaded with dichloromethane (10 ml)) using a gradient elution of hexane (50% to 0%) and ethyl acetate (50% to 100%) and also with methanol (5% in ethyl acetate) to yield the product as a light brown foam (770 mg).

$\delta_H$ (300 MHz, d$_6$DMSO) 7.65 (2H, d), 7.50 (2H, d), 6.95 (1H, s), 6.90 (2H, d), 6.80 (2H, d), 6.00 (2H, s), 4.10 (2H, t), 3.70 (2H, t), 1.15 (9H, s)

Preparation 22

Preparation of 2-({5-[{[4-(tert-butyl)phenyl]sulfonyl}(isobutoxycarbonyl)amino]-4-iodo-3-isoxazolyl}oxy)ethyl acetate

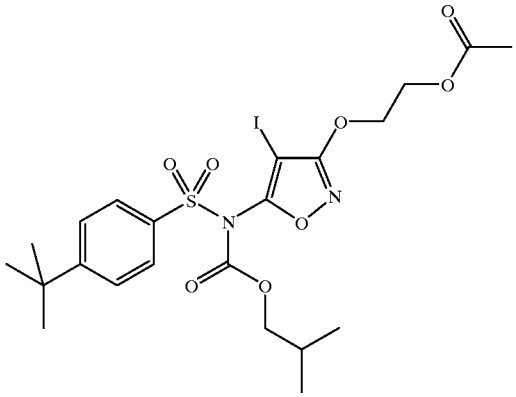

To a string solution of 2-{[5-({[4-(tert-butyl)phenyl]sulfonyl}amino)-4-iodo-3-isoxazolyl]oxy}ethyl acetate (Preparation 23) (9.44 g) in dichloromethane was added pyridine (1.65 ml) followed by the slow addition of isobutylchloroforomate (2.41 ml) over 10 minutes. The reaction mixture was stirred at room temperature for one hour. The solvent was removed in vacuo to yield the crude material. This was purified using column chromatography (300 g silica, compound loaded with dichloromethane (15 ml)) using a gradient elution of hexane (100% to 75%) and ethyl acetate (0% to 25%) to yield the desired compound as a yellow oil (7.70 g).

$\delta_H$ (300 MHz, CDCl$_3$) 8.05 (2H, d), 7.60 (2H, d), 4.50 (2H, m), 4.45 (2H, m), 3.90 (2H, d), 2.15 (3H, s), 1.85 (1H, m), 1.35 (9H, s), 0.80 (6H, d)

Preparation 23

Preparation of 2-{[5-({[4-(tert-butyl)phenyl]sulfonyl}amino)-4-iodo-3-isoxazolyl]oxy}ethyl acetate

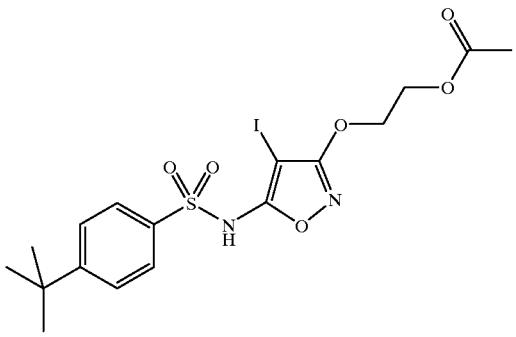

To a stirring solution of 2-{[5-({[4-(tert-butyl)phenyl]sulfonyl}amino)-3-isoxazolyl]oxy}ethyl acetate (Preparation 24) (1.17 g) in tetrahydrofuran (10 ml) was added N-iodosuccinimide (0.76 g). The reaction mixture was left stirring at room temperature overnight. The solvent was removed in vacuo to yield the crude material as a brown oil (1.5 g). The crude material was purified using the Biotage™ Flash 40i system (silica, 90 g) and eluted with hexane:ethyl acetate (1:9) to yield the product as a brown oil.

$\delta_H$ (300 MHz, CDCl$_3$) 7.90 (2H, d), 7.55 (2H, d), 4.35–4.45 (4H, m), 2.10 (3H, s), 1.35 (9H, s)

Preparation 24

Preparation of 2-{[5-({[4-(tert-butyl)phenyl]sulfonyl}amino)-3-isoxazolyl]oxy}ethyl acetate

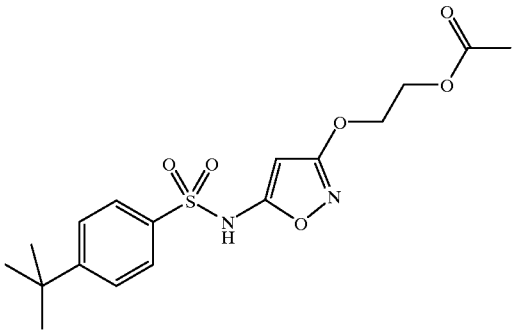

To a solution of tert-butyl 3-[2-(acetoxy)ethoxy]-5-({[4-(tert-butyl)phenyl]sulfonyl}amino)-4-isoxazolecarboxylate (Preparation 25) (3.16 g) in dichloromethane (40 ml) was added trifluoroacetic acid (20 ml). The reaction mixture was heated to reflux for 3 hours. After which time the reaction mixture was basified to pH8 using sodium hydrogen carbonate solution and then re-acidified to pH2 using aqueous hydrochloric acid (1.0M). This aqueous layer was extracted into ethyl acetate (2×250 ml) and the organics combined, dried over magnesium sulfate and the solvent removed in vacuo to yield the crude material (2.6 g). This was dissolved up in toluene and refluxed for 2 hours. The solvent was removed in vacuo to yield the crude material as a whitish brown solid (2.3 g). The crude material was purified using the Biotage™ Flash 40i system (silica, 90 g) and eluted with hexane:ethyl acetate (5:2) to yield the product as a white solid (1.2 g)

$\delta_H$ (300 MHz, CDCl$_3$) 7.80 (2H, d), 7.55 (2H, d), 5.65 (1H, s), 4.35–4.40 (4H, m), 2.10 (3H, s), 1.35 (9H, s)

Preparation 25

Preparation of tert-butyl 3-[2-(acetoxy)ethoxy]-5-({[4-(tert-butyl)phenyl]sulfonyl}amino)-4-isoxazolecarboxylate

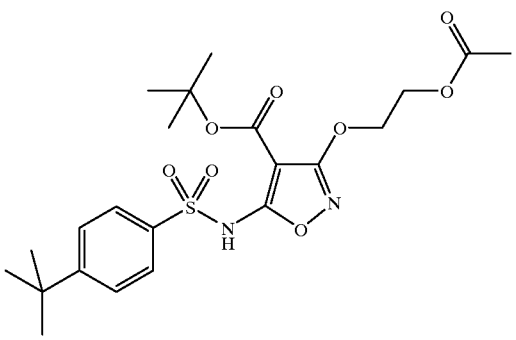

To a stirring solution of tert-butyl 3-[2-(acetoxy)ethoxy]-5-amino-4-isoxazolecarboxylate (Preparation 26) (6.0 g) in tetrahydrofuran (55 ml) under an atmosphere of nitrogen, was added sodium hydride (1.68 g of a 60% dispersion in oil). The reaction was stirred for 15 minutes after which time tert-butylbenzenesulfonyl chloride (5.14 g) was added. The reaction was stirred at room temperature overnight. The solvent was removed in-vacuo and redissolved in dichloromethane (50 ml) and then washed with water (50 mm with 3 drops of HCl). The organics were further washed with brine (40 ml), dried over magnesium sulfate and concentrated under reduced pressure to yield the crude material (7.0 g). The crude material was purified using the Biotage™ Flash 40i system (silica, 90 g) with a gradient elution of ethyl acetate (10% to 95%) and dichloromethane (90% to 5%) to yield the desired product as a white solid (3.5 g).

$\delta_H$ (300 MHz, d$_6$DMSO) 7.75 (2H, d), 7.45 (2H, d), 4.15–4.30 (4H, m), 2.00 (3H, s), 1.40 (9H, s), 1.30 (9H, s)

Preparation 26

Preparation of tert-butyl 3-[2-(acetoxy)ethoxy]-5-amino-4-isoxazolecarboxylate

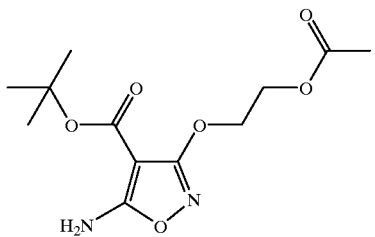

To a stirring solution of tert-butyl 5-amino-3-(2-hydroxyethoxy)-4-isoxazolecarboxylate (R. Neidlein, J.Heterocyclic Chem., 1989, 26,1335) (5.60 g) and triethylamine (3.36 ml) in tetrahydrofuran (50 ml) at room temperature was added dimethylaminopyridine (280 mg) followed by acetic anhydride (2.81 g). The reaction was stirred for 2 hours at room temperature. The solvent was removed in vacuo to yield the crude material (6.0 g). The crude material was purified using the Biotage™ Flash 40i System (silica, 90 g), eluting with ethyl acetate:hexane (1:1) to yield the product as an off white solid (5.0 g)

$\delta_H$ (300 MHz, CDCl$_3$) 5.80 (2H, brs), 4.40–4.45 (4H, m), 2.10 (3H, s), 1.55 (9H, s);

What is claimed is:

1. A process for making compounds of formula (I)

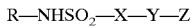

R—NHSO$_2$—X—Y—Z     (I)

wherein
R is an organic radical;
X is selected from
  a) 5–6 membered monocyclic aromatic ring optionally containing one or two heteroatoms, each independently selected from O, N and S;
  b) a C$_1$–C$_6$ alkylene group, straight or branched; and
  c) a direct link;
Y is —C(CH$_3$)$_2$— or —CH(CH$_3$)—; and
Z is —CH$_2$OH or —COOH;
which comprises oxidising a compound of formula (II)

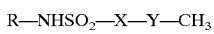

R—NHSO$_2$—X—Y—CH$_3$     (II)

with a cytochrome P450 enzyme.

2. The process of claim 1, wherein the cytochrome P450 enzyme is contained within a microorganism.

3. The process of claim 2, wherein the microorganism containing the cytochrome P450 enzyme is a unicellular bacteria, a filamentous bacteria or a filamentous fungi.

4. The process of claim 1, wherein R is a a 5–6 membered monocyclic aromatic ring optionally containing one or two heteroatoms, each independently selected from O, N and S, said ring being optionally further substituted.

5. The process of claim 4, wherein R is selected from the group consisting of:

3-[2-(5-bromopyrimidin-2-yl)oxyethoxy]-1-methyl-4-p-tolylpyrazol-5-yl,
4-[2-(5-bromopyrimidin-2-yl)oxyethoxy]-5-p-tolylpyrimidin-6-yl,
4-(2-hydroxyethoxy)-5-(2-methoxyphenoxy)-2-(2-pyrimidinyl)pyrimidin-6-yl,
4-methoxy-5-(2-methoxyphenoxy)-2-(2-pyrimidinyl)pyrimidin-6-yl,
3-(2-ethoxyethoxy)-1-methyl-4-p-tolylpyrazol-5-yl,
4-(1,3-benzodioxol-5-yl)-3-[2-(5-chloropyrimidin-2-yl)oxyethoxy]-1-methylpyrazol-5-yl,
4-(1,3-benzodioxol-5yl)-3-(2-hydroxyethoxy)-1-methylpyrazol-5-yl,
4-(1,3-benzodioxol-5-yl)-3-[2-(5-bromopyrimidin-2-yl)oxyethoxy]isoxazol-5-yl,
1-methyl-3-(2-methoxyethoxy)-4-p-tolylpyrazol-5-yl, and
3-(2-ethoxyethoxy)-1-methyl-4-p-tolylpyrazol-5-yl.

6. The process of claim 1, wherein Z is —CH$_2$OH.

7. The process of claim 6, wherein Y is —C(CH$_3$)$_2$—.

8. The process of claim 7, wherein X is phenylene, pyridylene, ethylene or propylene.

9. The process of claim 8, wherein X is 1,4-phenylene.

10. The process of claim 9, wherein R is selected from the group consisting of:

3-[2-(5-bromopyrimidin-2-yl)oxyethoxy]-1-methyl-4-p-tolylpyrazol-5-yl,
4-[2-(5-bromopyrimidin-2-yl)oxyethoxy]-5-p-tolylpyrimidin-6-yl,
4-(2-hydroxyethoxy)-5-(2-methoxyphenoxy)-2-(2-pyrimidinyl)pyrimidin-6-yl,
4-methoxy-5-(2-methoxyphenoxy)-2-(2-pyrimidinyl)pyrimidin-6-yl,
3-(2-ethoxyethoxy)-1-methyl-4-p-tolylpyrazol-5-yl,
4-(1,3-benzodioxol-5-yl)-3-[2-(5-chloropyrimidin-2-yl)oxyethoxy]-1-methylpyrazol-5-yl,
4-(1,3-benzodioxol-5yl)-3-(2-hydroxyethoxy)-1-methylpyrazol-5-yl, and
4-(1,3-benzodioxol-5-yl)-3-[2-(5-bromopyrimidin-2-yl)oxyethoxy]isoxazol-5-yl.

11. The process of claim 6 wherein a compound of formula (II) is treated with one of Streptomyces lavendulae ATCC14159, Streptomyces sp. PTA-1685, Streptomyces cyaneus PTA-1686, Streptomyces lydicus PTA-1687, Streptomyces griseus ATCC55070, Streptomyces griseolus ATCC11796, Amyclatopsis orientalis ATCC19795, Streptomyces griseus subsp. griseus ATCC13273, Streptomyces argentolus ATCC11009, Nocardia meditteranei ATCC21271, Streptomyces fumanus ATCC19904, Amycoloata autotrophica ATCC35203, Streptomyces rimosus subsp. rimosus ATCC10970, Streptomyces griseus subsp. griseus ATCC10137, Streptomyces sp. ATCC31273, Cunninghamella echinulata var. elegans ATCC8688a, Mortierella isabellina ATCC42613, Verticillium lecanii ATCC60540, Mucor circinelloides ATCC7941, Cunninghamella echinulata var. echinulata ATCC36190, Syncephalastrum racemosum ATCC18192, Beauvaria sulphurescens ATCC7159, *Absidia pseudocylindrospora* ATCC24169, *Amycolata autotrophica* ATCC13181, *Rhodococcus rhodochrous* ATCC12674, *Rhodococcus rhodochrous* ATCC19067, *Bacillus megaterium* ATCC14581, *Bacillus megaterium* ATCC13368, Rhodococcus sp. ATCC19070, Actinomyces sp. ATCC53828, *Bacillus subtilis* ATCC55060, *Pseudomonas putida* ATCC17453, *Pseudomonas putida* ATCC49451, *Bacillus sphaericus* ATCC10208, *Rhizopus oryzae* ATCC11145, *Absidia blakesleeeana* ATCC10148a, *Sepedonium chrysospermum* ATCC13378, *Alcaligenes eutrophus* ATCC17697, *Streptomyces galilaeus* ATCC31133, *Actinoplanes missouriensis* ATCC23342, *Actinoplanes missouriensis* ATCC14538, *Streptomyces peucetius* subsp. *caesius* ATCC27952, *Streptomyces lincolnensis* ATCC25466, *Streptomyces bambergiensis* ATCC 13879, *Streptomyces argillaceus* ATCC12956, *Streptomyces albogriseolus* ATCC31422, *Streptomyces rutgersensis* ATCC3350, *Corynebacterium hydrocarboxydans* ATCC21767, *Streptomyces fradiae* ATCC10745, *Streptomyces hydrogenans* ATCC19631, Unidentified bacterium ATCC13930, Actinoplanes sp. ATCC53771, *Thamnidium elegans* ATCC18191, *Aspergillus terreus* ATCC10020, *Curvularia lunata* ATCC13432, *Emericalla unguis* ATCC13431, *Epicoccum humicola* ATCC12722, *Rhodococcus chlorophenolicus* ATCC49826, *Aspergillus ochraceus* ATCC18500, *Pithomyces cynodontis* ATCC26150, *Streptomyces roseochromogenes* ATCC13400, *Streptomyces griseus* subsp. *autotrophica* ATCC53668, *Streptomyces griseus* subsp. *griseus* ATCC23337, *Absidia repens* ATCC14849 and *Aspergillus alliaceus* ATCC10060.

12. The process of claim 10, wherein R is 3-[2-(5-bromopyrimidin-2-yl)oxyethoxy]-1-methyl-4-p-tolylpyrazol-5-yl.

13. The process of claim 12, wherein the micro-organism is selected from one of *Syncephalastrum racemosum* ATCC18192, Streptomyces sp. PTA-1685, *Streptomyces lavendulae* ATCC14159, *Streptomyces cyaneus* PTA-1686, *Streptomyces griseus* ATCC55070, *Amycolatopsis orientalis* ATCC19795, *Streptomyces argentolus* ATCC11009, *Nocardia meditteranei* ATCC21271, *Streptomyces fumanus* ATCC19904, *Streptomyces rimosus* subsp. *rimosus* ATCC10970, *Streptomyces griseus* ATCC10137, *Cunninghamella echinulata* ATCC8688a, *Mortierella isabellina* ATCC42613, *Verticillium lecanii* ATCC60540, *Mucor circinelloides* ATCC7941 and *Cunninghamella echinulata* ATCC10028b.

14. The process of claim 10, wherein R is 4-[2-(5-bromopyrimidin-2-yl)oxyethoxy]-5-p-tolylpyrimidin-6-yl.

15. The process of claim 14, wherein the micro-organism is selected from one of *Streptomyces lavendulae* ATCC14159, Streptomyces sp. PTA-1685, *Streptomyces cyaneus* PTA-1686, *Streptomyces lydicus* PTA-1687, *Streptomyces griseus* ATCC55070, *Streptomyces griseolus* ATCC11796, *Amyclatopsis orientalis* ATCC19795, *Streptomyces griseus* subsp. *griseus* ATCC13273, *Streptomyces fumanus* ATCC19904, *Amycoloata autotrophica* ATCC35203, *Streptomyces griseus* subsp. *griseus* ATCC10137, Streptomyces sp. ATCC31273, *Mortierella isabellina* ATCC42613, *Verticillium lecanii* ATCC60540, *Mucor circinelloides* ATCC7941, *Cunninghamella echinulata* var. *echinulata* ATCC36190, *Syncephalastrum racemosum* ATCC18192, *Amycolata autotrophica* ATCC13181, *Rhodococcus rhodochrous* ATCC12674, *Rhodococcus rhodochrous* ATCC19067, *Bacillus megaterium* ATCC14581, *Bacillus megaterium* ATCC13368, Rhodococcus sp. ATCC19070, Actinomyces sp. ATCC53828, *Bacillus subtilis* ATCC5506, *Pseudomonas putida* ATCC49451, *Bacillus sphaericus* ATCC10208, *Rhizopus oryzae* ATCC11145, *Absidia blakesleeeana* ATCC10148a, *Sepedonium chrysospermum* ATCC13378, *Alcaligenes eutrophus* ATCC17697, *Streptomyces galilaeus* ATCC31133, *Actinoplanes missouriensis* ATCC23342, *Actinoplanes missouriensis* ATCC14538, *Streptomyces peucetius* subsp. *caesius* ATCC27952, *Streptomyces lincolnensis* ATCC25466, *Streptomyces bambergiensis* ATCC13879, *Streptomyces argillaceus* ATCC12956, *Streptomyces albogriseolus* ATCC31422, *Streptomyces rutgersensis* ATCC3350, *Corynebacterium hydrocarboxydans* ATCC21767, *Streptomyces fradiae* ATCC10745, *Streptomyces hydrogenans* ATCC19631, Unidentified bacterium ATCC13930, Actinoplanes sp. ATCC53771, *Thamnidium elegans* ATCC18191, *Aspergillus terreus* ATCC10020, *Curvularia lunata* ATCC13432, *Emericalla unguis* ATCC13431 *Epicoccum humicola* ATCC12722, *Rhodococcus chlorophenolicus* ATCC49826, *Aspergillus ochraceus* ATCC18500, *Streptomyces roseochromogenes* ATCC13400, *Streptomyces griseus* subsp. *autotrophica* ATCC53668, *Streptomyces griseus* subsp. *griseus* ATCC23337, *Absidia repens* ATCC14849 and *Aspergillus alliaceus* ATCC10060.

16. The process of claim 10, wherein R is 4-(2-hydroxyethoxy)-5-(2-methoxyphenoxy)-2-(2-pyrimidinyl)pyrimidin-6-yl.

17. The process of claim 16, wherein the micro-organism is selected from one of *Streptomyces rimosus* subsp. *rimosus* ATCC10970, *S.fumanus* ATCC19904, *Streptomyces argentolus* ATCC11009, *Bacillus megaterium* ATCC14538, *Streptomyces griseus* ATCC13273, *Streptomyces griseus* ATCC10137, *Streptomyces griseolus* ATCC11796, *Streptomyces lavendulae* ATCC14159, *Streptomyces cyaneus* PTA-1686, Streptomyces sp. PTA-1685, *Amycolata autotrophica* ATCC13181, *Amycolata autotrophica* ATCC35203 and *Mortierella isabellina* ATCC42613.

18. The process of claim 10, wherein R is 4-(1,3-benzodioxol-5-yl)-3-[2-(5-bromopyrimidin-2-yl)oxyethoxy]isoxazol-5-yl.

19. The process of claim 18, wherein the micro-organism is selected from one of *Streptomyces rimosus* subsp. *rimosus* ATCC10970, *Streptomyces fumanus* ATCC19904, *Streptomyces argentolus* ATCC11009, *Bacillus megaterium* ATCC14538, *Streptomyces griseus* ATCC13273, *Streptomyces griseus* ATCC10137, *Streptomyces griseolus* ATCC11796, *Streptomyces lavendulae* ATCC14159, *Streptomyces cyaneus* PTA-1686, Streptomyces sp. PTA-1685, *Amycolata autotrophica* ATCC13181, *Amycolata autotrophica* ATCC35203 and *Mortierella isabellina* ATCC42613.

20. The process of claim 6, wherein Y is —CH(CH$_3$)—.

21. The process of claim 20, wherein X is phenylene, pyridylene, ethylene or propylene.

22. The process of claim 21, wherein X is 2,5-pyridylene, wherein Y is at the 2-position.

23. The process of claim 22, wherein R is 4-(1,3-benzodioxol-5-yl)-3-[2-(5-chloropyrimidin-2-yl)oxyethoxy]-1-methylpyrazol-5-yl.

24. The process of claim 20, wherein a compound of formula (II) is treated with one of *Streptomyces lavendulae* ATCC14159, Streptomyces sp. PTA-1685, *Streptomyces cyaneus* PTA-1686, *Streptomyces lydicus* PTA-1687, *Streptomyces griseus* ATCC55070, *Streptomyces griseolus* ATCC11796, *Amyclatopsis orientalis* ATCC19795, *Streptomyces griseus* subsp. *griseus* ATCC13273, *Streptomyces argentolus* ATCC11009, *Nocardia meditteranei* ATCC21271, *Streptomyces fumanus* ATCC19904, *Amycolata autotrophica* ATCC35203, *Streptomyces rimosus* subsp.

*rimosus* ATCC10970, *Streptomyces griseus* subsp. *griseus* ATCC10137, Streptomyces sp. ATCC31273, *Cunninghamella echinulata* var. *elegans* ATCC8688a, *Mortierella isabellina* ATCC42613, *Verticillium lecanii* ATCC60540, *Mucor circinelloides* ATCC7941, *Cunninghamella echinulata* var. *echinulata* ATCC36190, *Syncephalastrum racemosum* ATCC18192, *Beauvaria sulphurescens* ATCC7159, *Absidia pseudocylindrospora* ATCC24169, *Amycolata autotrophica* ATCC13181, *Rhodococcus rhodochrous* ATCC12674, *Rhodococcus rhodochrous* ATCC19067, *Bacillus megaterium* ATCC14581, *Bacillus megaterium* ATCC13368, Rhodococcus sp. ATCC19070, Actinomyces sp. ATCC53828, *Bacillus subtilis* ATCC55060, *Pseudomonas putida* ATCC17453, *Pseudomonas putida* ATCC49451, *Bacillus sphaericus* ATCC10208, *Rhizopus oryzae* ATCC11145, *Absidia blakesleeeana* ATCC10148a, *Sepedonium chrysospermum* ATCC13378, *Alcaligenes eutrophus* ATCC17697, *Streptomyces galilaeus* ATCC31133, *Actinoplanes missouriensis* ATCC23342, *Actinoplanes missouriensis* ATCC14538, *Streptomyces peucetius* subsp. *caesius* ATCC27952, *Streptomyces lincolnensis* ATCC25466, *Streptomyces bambergiensis* ATCC13879, *Streptomyces argillaceus* ATCC12956, *Streptomyces albogriseolus* ATCC31422, *Streptomyces rutgersensis* ATCC3350, *Corynebacterium hydrocarboxydans* ATCC21767, *Streptomyces fradiae* ATCC10745, *Streptomyces hydrogenans* ATCC19631, Unidentified bacterium ATCC13930, Actinoplanes sp. ATCC53771, *Thamnidium elegans* ATCC18191, *Aspergillus terreus* ATCC10020, *Curvularia lunata* ATCC13432, *Emericalla unguis* ATCC13431, *Epicoccum humicola* ATCC12722, *Rhodococcus chlorophenolicus* ATCC49826, *Aspergillus ochraceus* ATCC18500, *Pithomyces cynodontis* ATCC26150, *Streptomyces roseochromogenes* ATCC13400, *Streptomyces griseus* subsp. *autotrophica* ATCC53668, *Streptomyces griseus* subsp. *griseus* ATCC23337, *Absidia repens* ATCC14849 and *Aspergillus alliaceus* ATCC10060.

25. The process claim 1, wherein Z is —COOH.

26. The process of claim 25, wherein Y is —C(CH$_3$)$_2$—.

27. The process of claim 26, wherein X is phenylene, pyridylene, ethylene or propylene.

28. The process of claim 27, wherein X is 1,4-phenylene.

29. The process of claim 28 where R is selected from the group consisting of:

3-[2-(5-bromopyrimidin-2-yl)oxyethoxy]-1-methyl-4-p-tolylpyrazol-5-yl,

4-[2-(5-bromopyrimidin-2-yl)oxyethoxy]-5-p-tolyl-pyrimidin-6-yl, 1-methyl-3-(2-methoxyethoxy)-4-p-tolylpyrazol-5-yl, and 3-(2-ethoxyethoxy)-1-methyl-4-p-tolylpyrazol-5-yl.

30. The process of claim 26, wherein a compound of formula (II) is treated with one of *Amycolata autotrophica* ATCC 35203, *Nocardia meditteranei* ATCC21271, *Amycolatopsis orientalis* ATCC19795, *Streptomyces griseolus* ATCC11796, *Streptomyces rimosus* subsp. *rimosus* ATCC10970 and *Nocardia meditteranei* ATCC21271.

31. The process of claim 29, wherein R is 3-[2-(5-bromopyrimidin-2-yl)oxyethoxy]-1-methyl-4-p-tolylpyrazol-5-yl.

32. The process of claim 31, wherein the micro-organism is selected from the group consisting of *Amycolata autotrophica* ATCC 35203, *Nocardia meditteranei* ATCC21271 and *Amycolatopsis orientalis* ATCC19795.

33. The process of claim 29, wherein R is 4-[2-(5-bromopyrimidin-2-yl)oxyethoxy]-5-p-tolyl-pyrimidin-6-yl.

34. The process of claim 33, wherein the micro-organism is selected from the group consisting of *Streptomyces griseolus* ATCC11796, *Streptomyces rimosus* subsp. *rimosus* ATCC10970 and *Nocardia meditteranei* ATCC21271.

35. The process of claim 29, wherein R is 4-(1,3-benzodioxol-5-yl)-3-[2-(5-bromopyrimidin-2-yl)oxyethoxy]isoxazol-5-yl.

36. The process of claim 35, wherein the micro-organism is selected from the group consisting of *Streptomyces rimosus* subsp. *rimosus* ATCC10970, *Streptomyces fumanus* ATCC19904, *Streptomyces argentolus* ATCC11009, *Bacillus megaterium* ATCC14538, *Streptomyces griseus* ATCC13273, *Streptomyces griseus* ATCC10137, *Streptomyces griseolus* ATCC11796, *Streptomyces lavendulae* ATCC14159, *Streptomyces cyaneus* PTA-1686, Streptomyces sp. PTA-1685, *Amycolata autotrophica* ATCC13181, *Amycolata autotrophica* ATCC35203 and *Mortierella isabellina* ATCC42613.

37. The process of claim 25, wherein Y is —CH(CH$_3$)—.

38. The process of claim 37, wherein X is phenylene, pyridylene, ethylene or propylene.

39. The process of claim 38, wherein X is 2,5-pyridylene, wherein Y is at the 2-position.

40. The process of claim 37, wherein a compound of formula II is treated with one of *Amycolata autotrophica* ATCC 35203, *Nocardia meditteranei* ATCC21271, *Amycolatopsis orientalis* ATCC19795, *Streptomyces griseolus* ATCC11796, *Streptomyces rimosus* subsp. *rimosus* ATCC10970 and *Nocardia rheditteranei* ATCC21271.

* * * * *